United States Patent [19]
Yahara et al.

[11] Patent Number: 5,407,819
[45] Date of Patent: Apr. 18, 1995

[54] HUMAN PLASMINOGEN ACTIVATOR VARIANTS HAVING AMINO ACIDS 37-42 SUBSTITUTED AND A METHOD FOR THEIR MANUFACTURE

[75] Inventors: Hitoshi Yahara, Kakogawa; Tetsuya Nagaoka, Takasago; Kazuyoshi Yajima, Kobe; Yasuhiro Inenaka, Akashi; Keiji Matsumoto, Nishinomiya; Tetsu Kakutani, Kakogawa, all of Japan

[73] Assignee: Kanegafuchi Kagaku Kogyo Kabushiki Kaisha, Osaka, Japan

[21] Appl. No.: 869,380

[22] Filed: Apr. 16, 1992

Related U.S. Application Data

[63] Continuation-in-part of Ser. No. 585,004, Sep. 19, 1990, abandoned.

[30] Foreign Application Priority Data

| | | |
|---|---|---|
| Sep. 20, 1989 [JP] | Japan | 1-243750 |
| Oct. 17, 1989 [JP] | Japan | 1-269406 |
| Mar. 1, 1990 [JP] | Japan | 2-50428 |
| Aug. 2, 1990 [JP] | Japan | 2-206458 |

[51] Int. Cl.$^6$ .............. C12N 5/00; C12N 15/00; C12N 15/58; A61K 37/547
[52] U.S. Cl. .............. 435/226; 435/212; 435/240.2; 435/320.1; 536/23.2
[58] Field of Search ............ 435/212, 219, 226, 320.1, 435/240.2, 252.3, 69.1; 536/23.5, 23.2

[56] References Cited

PUBLICATIONS

"Cloning and Expression of Human Tissue-Type Plasminogen Activator cDNA in E. coli", D. Pennica, et al., Nature, vol. 301, Jan. 20, 1983, pp. 214–221.

"Recombinant Tissue Plasminogen Activator: A Brief Review", E. B. Grossbard, Pharmaceutical Research, vol. 4, No. 5, 1987, pp. 375–378.

"Catabolism of Human Tissue Plasminogen Activator in Mice", H. E. Fuchs, et al., Blood. vol. 65, No. 3, Mar. 1985, pp. 539–544.

"Coronary Thrombolysis in Dogs with Intravenously Administered Human Prourokinase", D. Collen, et al., Circulation, vol. 72, No. 2, Aug. 1985, pp. 384–388.

"A Tissue-Type Plasminogen Activator Mutant with Prolonged Clearance in Vivo", M. J. Browne, et al., The Journal of Biological Chemistry, vol. 263, No. 4, Feb. 5, 1988, pp. 1599–1602.

"Isolation, Identification and Pharmacokinetic Properties of Human Tissue-type Plasminogen activator Species: Possible Localisation of a Clearance Recognition Site", I. Dodd, et al. Thrombosis and Haemostasis, vol. 59, No. 3, 1988, pp. 523–528.

"Structure-Function Analysis with Tissue-Type Plasminogen Activator", N. K. Kalyan, et al., The Journal of Biological Chemistry, vol. 263, No. 8, Mar. 15, 1988, pp. 3971–3978.

"Variants of Human Tissue-type Plasminogen Activator", G. R. Lansen, et al., The Journal of Biological Chemistry, vol. 263, No. 2, Jan. 15, 1988, pp. 1023–1029.

"Functional Effects of Asparagine-linked Oligosaccharide on Natural and Variant Human Tissue-type Plasminogen Activator", L. Hansen, et al., The Journal of Biological Chemistry, vol. 263, No. 30, Oct. 25, 1988, pp. 15713–15719.

"Pharmacokinetics and Thrombolytic Properties of Deletion Mutants of Human Tissue-Type Plasminogen (List continued on next page.)

Primary Examiner—Robert J. Hill, Jr.
Assistant Examiner—Marianne Porta Allen
Attorney, Agent, or Firm—Fay, Sharpe, Beall, Fagan, Minnich & McKee

[57] ABSTRACT

A TPA variant with replacement of amino acids is provided. In a typical embodiment, the variant has an amino acid sequence with replacement of the amino acid group consisting of asparagine at the 37th position, serine at the 38th position, glycine at the 39th position, arginine at the 40th position, alanine at the 41st position, and glutamine at the 42nd position from the N-terminus of the amino acid sequence of mature human tissue plasminogen activator.

13 Claims, 14 Drawing Sheets

OTHER PUBLICATIONS

Activator in Rabbits", D. Collen, et al., Blood, vol. 71, Jan., 1988, pp. 216–219.

"On the Interaction of the Finger and the Kringle-2 Domain of Tissue-type Plasminogen Activator with Fabrin", A. J. Zonneveld, et al., The Journal of Biological Chemistry, vol. 261, No. 30, Oct. 25, 1986, 1983, pp. 14214–14218.

"Continuous Production of Erythropoietin by an Established Human Renal Carcinoma Cell Line: Development of the Cell Line", J. B. Sherwood, et al., Proc. Natl. Acad. Sci. USA, vol. 83, Jan., 1986, pp. 165–169.

"Biological and Functional Characterization of Human Tissue-Type Plasminogen Activator Variants With Mutagenized Kringle Domains", Collen et al, The Journal of Biological Chemistry, vol. 265, No. 21, Jul. 25, 1990, pp. 12184–12191.

(1) Synthetic DNA fragment

5' GATCTTACCAAGTGATCTGCAAGAAGAAGAAAACGCAGATGATATACCAGCAACATCAGTCATG 3'
5' ACTGATGTTGCTGGTATATCATCTGCGTTTTCTTCTTCTTGCAGATCACTTGGTAA 3'

HUMAN PLASMINOGEN ACTIVATOR VARIANTS HAVING AMINO ACIDS 37-42 SUBSTITUTED AND A METHOD FOR THEIR MANUFACTURE

This is a continuation-in-part of copending application Ser. No. 07/585,004, filed on Sep. 19, 1990, now abandoned.

BACKGROUND OF THE INVENTION

1. Field of the Invention

The present invention relates to a human tissue plasminogen activator variant which is useful in the treatment of thrombosis; a DNA sequence encoding the said plasminogen activator; an expression vector comprising the said DNA sequence; a transformant into which the said vector has been introduced; and a method for producing the said plasminogen activator.

2. Description of the Prior Art

Concerning mature human tissue plasminogen activator (hereinafter, referred to as TPA), particularly detailed research has been devoted to TPA secreted by human melanoma (i.e., Bowes melanoma) cells, and TPA is known to be a glycoprotein comprising 572 amino acid residues [Pennica, D., et al., Nature, 301, 214 (1983)].

TPA is an enzyme which acts upon the plasminogen which is present in the blood and converts this plasminogen into plasmin. The plasmin dissolves the fibrin which causes thrombi. TPA possesses strong affinity with fibrin, moreover, the activity of TPA is fibrin-dependent, hence, TPA is regarded as acting specifically upon thrombi. Therefore, TPA is used therapeutically for the treatment of various types of thrombosis [Grossbard, E. B., Pharmaceutical Research, 4, 375 (1987)]. However, when TPA is administered into the blood stream for the treatment of thrombosis, long-sustained effect is not obtained, and the TPA rapidly clears from the circulation, which constitutes a problem in therapeutic applications. TPA is believed to be metabolized principally in the liver [Fuchs, H. E., et al., Blood, 65, 539 (1985)]. The half-life of TPA in the blood is only about 2 minutes [Collen, D., et al., Circulation, 72, 384 (1985)]. Therefore, rather large quantities of protein are currently administered by continuous infusion to maintain therapeutic plasma levels. A TPA with longer in vivo half-life might permit a single bolus injection, the use of lower doses, and thereby, lower cost for the treatment.

With a view to solving these problems, various types of TPA variants, with longer half-life in vivo obtained by chemical or enzymatic modification or by genetic engineering methods, have been reported in the literature [Browne, M. J., et al., J. Biol. Chem., 263, 1599 (1988); Dodd, I., et al., Thrombosis and Haemostasis, 59, 523 (1988); Kayan, N. K., et al., J. Biol. Chem., 263, 3971 (1988)]. However, although greatly improved with respect to plasma half-life in vivo, the TPA variants described in these reports have proved to be extremely inferior to the TPA with regard to the affinity with fibrin that is one of the characteristic properties of TPA [Larsen, G. R., et al., J. Biol. Chem., 263, 1023 (1988)]. Furthermore, in some case, these TPA variants also display a pronounced decrease in fibrinolytic ability [Hansen, L., et al., J. Biol. Chem., 263, 15713 (1988)].

Thus, TPA variants with superior therapeutic efficacy have not yet been obtained. Therefore, there has existed a need for the development of TPA variants which permit effective treatment of thrombosis with small doses by virtue of slow clearance; retain the original biochemical characteristics of TPA to the greatest possible extent; and cause no significant increases in hemorrhagic or other adverse side effects.

TPA is composed of five regions, i.e., a finger region, a growth factor region, a kringle 1 region, a kringle 2 region, and a region possessing serine protease activity. These regions are aligned in the above-mentioned order from the N-terminus of the amino acid sequence of TPA (Pennica, D., et. al., Nature, 301, 214, supra ). Many of the TPA variants with longer half-life in vivo created thus far, lack the finger region alone, or lack an extensive region including finger region and other regions [Hansen, L., et al., J. Biol. Chem., 263, 15713, supra; Larsen, G. R., et al., J. Biol. Chem., 263, 1023, supra; and Collen, D., et al., Blood, 71, 219 (1988)]. These types of TPA variants, lacking the finger region, are improved with respect to persistence in the blood, but display markedly decreased thrombolytic ability. Therefore, plasminogen activation and fibrolytic properties are believed to arise from the finger region.

The aforesaid kringle regions have also been studied. The kringle 2 region is said to be concerned in the affinity of TPA for fibrin and the property of activation of TPA by fibrin. On the other hand, although derivatives lacking the kringle 1 region have been created and studied, the function of this region has not yet been adequately clarified [Zonneveld, A. J. V., et al., Journal of Biological Chemistry, 261, 14214 (1986); Proc. N. A. S., 83, 169 (1986) ].

SUMMARY OF THE INVENTION

The present inventors endeavored to create TPA variants (hereinafter reffered to as VPAs) characterized by long persistence in the blood and high affinity for plasminogen by appropriately modifying the finger region without loss of the essential characteristics of this region, or by modifying the kringle regions, or by modifying both the finger and kringle regions. Moreover, with the objective of enhancing the affinity for fibrin and the property of activation by fibrin which are possessed by the kringle 2 region, the amino acid sequence of the kringle 1 region was converted into a sequence resembling the kringle 2 region. In this manner, using genetic engineering methods, a large number of amino acid substitution products were created. As a result, among a number of VPAs with the 37th through 42nd amino acids included in the finger region replaced by other amino acids, especially by hydrophobic amino acids, and/or the amino acids of a portion of the kringle 1 region replaced by other prescribed amino acids, certain particular VPAs were found to possess nearly the same degree of thrombolytic effectiveness as TPA, and, moreover, to display greatly extended half-life in vivo, thereby realizing the completion of the present invention.

The TPA variant (reffered to as VPA) which overcomes the above-discussed and numerous other disadvantages and deficiencies of the prior art, is a plasminogen activator in which the amino acid group consisting of asparagine at the 37th position, serine at the 38th position, glycine at the 39th position, arginine at the 40th position, alanine at the 41st position, and glutamine at the 42nd position from the N-terminus of the amino acid sequence of TPA is replaced by a hydrophobic amino acid.

In a preferred embodiment, the hydrophobic amino acid is selected from the group consisting of phenylalanine, valine, isoleucine, leucine, and serine.

The VPA of this invention is a plasminogen activator in which glycine at the 161st position, lysine at the 162nd position, and serine at the 165th position from the N-terminus of the amino acid sequence of TPA are replaced by arginine, arginine, and tryptophan, respectively.

VPA of this invention is a plasminogen activator in which asparagine at the 37th position, serine at the 38th position, glycine at the 39th position, arginine at the 40th position, alanine at the 41st position, glutamine at the 42nd position, glycine at the 161st position, lysine at the 162nd position, and serine at the 165th position from the N-terminus of TPA are replaced by serine, valine, valine, glutamic acid, phenylalanine, serine, arginine, arginine, and tryptophan, respectively.

VPA of this invention is a plasminogen activator in which asparagine at the 37th position, serine at the 38th position, glycine at the 39th position, arginine at the 40th position, alanine at the 41st position, glutamine at the 42nd position, and asparagine at the 115th position from the N-terminus of TPA are replaced by serine, valine, valine, glutamic acid, phenylalanine, serine, and proline, respectively.

The DNA sequence of this invention encodes the above-mentioned VPA.

In a preferred embodiment, the DNA sequence is derived from cDNA or genomic DNA.

The expression vector of this invention comprises the above-mentioned DNA sequence.

The transformant of this invention is obtained by introducing the above-mentioned expression vector into a cultured animal cell.

The glycosylated VPA of this invention is obtained by cultivating the transformant.

The method for producing a TPA of this invention comprises the steps of:

(a) constructing an expression vector which comprises the above-mentioned DNA sequence, (b) introducing said expression vector into a cultured animal cell, resulting in a transformant, (c) cultivating said transformant to produce a VPA, and (d) recovering the produced VPA.

Thus, the invention described herein makes possible the objectives of, (1) providing a VPA characterized by long half-life in vivo and high fibrinolyric ability; (2) providing a novel VPA which can be effectively used for the treatment of thrombotic disorders such as myocardial infarction by virtue of far improved half-life in vivo as compared with TPA as well as retention of the same level of thrombolytic ability as TPA; (3) providing a novel high-potency VPA which permit the improvement of the therapeutic efficacy of TPA treatment now being undertaken in connection with various vascular disorders; (4) providing a DNA sequence encoding the VPA possessing the aforesaid superior properties, an expression vector containing the said DNA sequence, and a transformant obtained by the introduction of the said expression vectors; and (5) providing a method for producing a VPA by cultivation of the said transformant.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
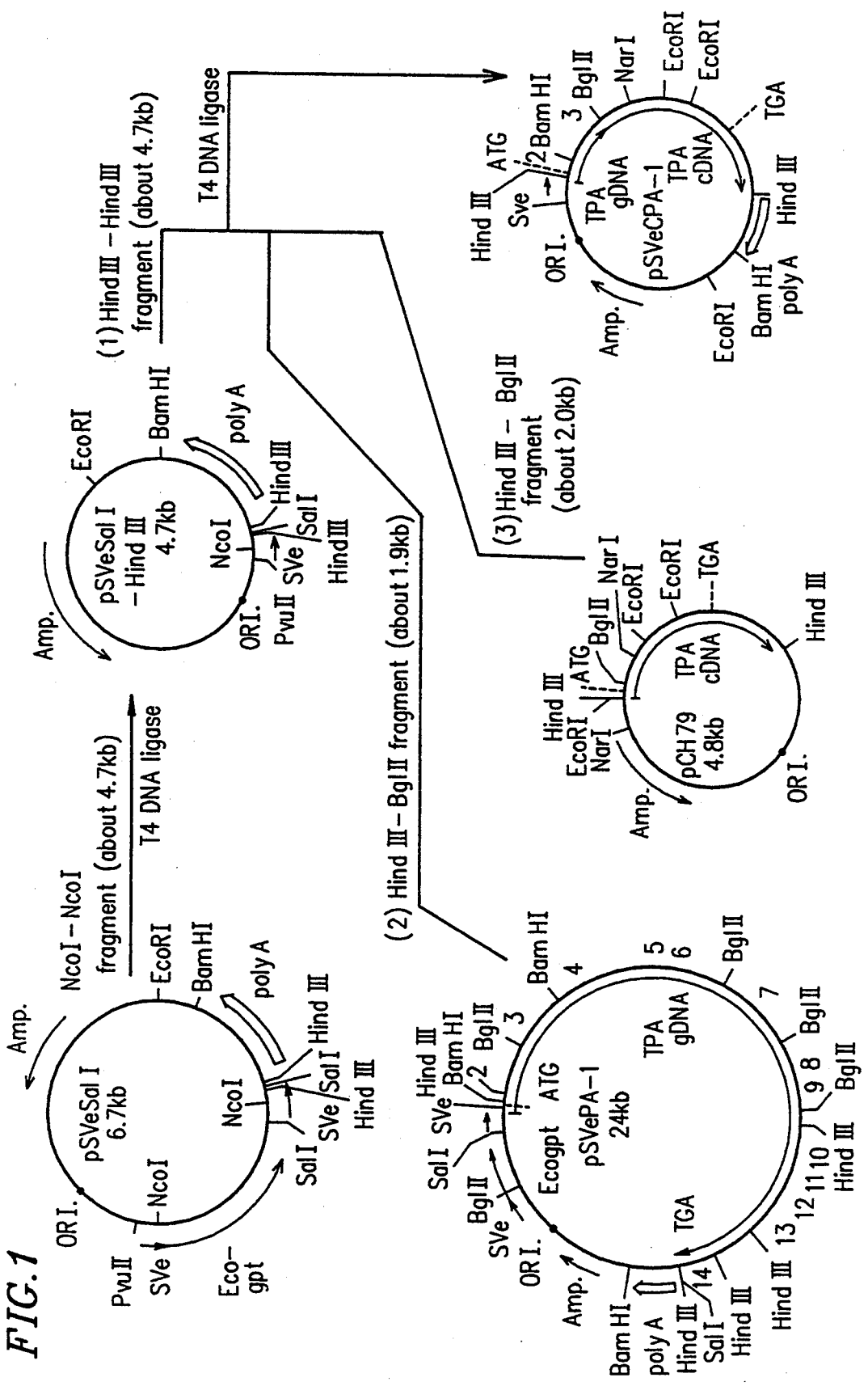
FIG. 1 is a schematic diagram showing the construction of the TPA expression vector pSVeCPA-1 used for the construction of expression vectors of the present invention.
Figure 2:
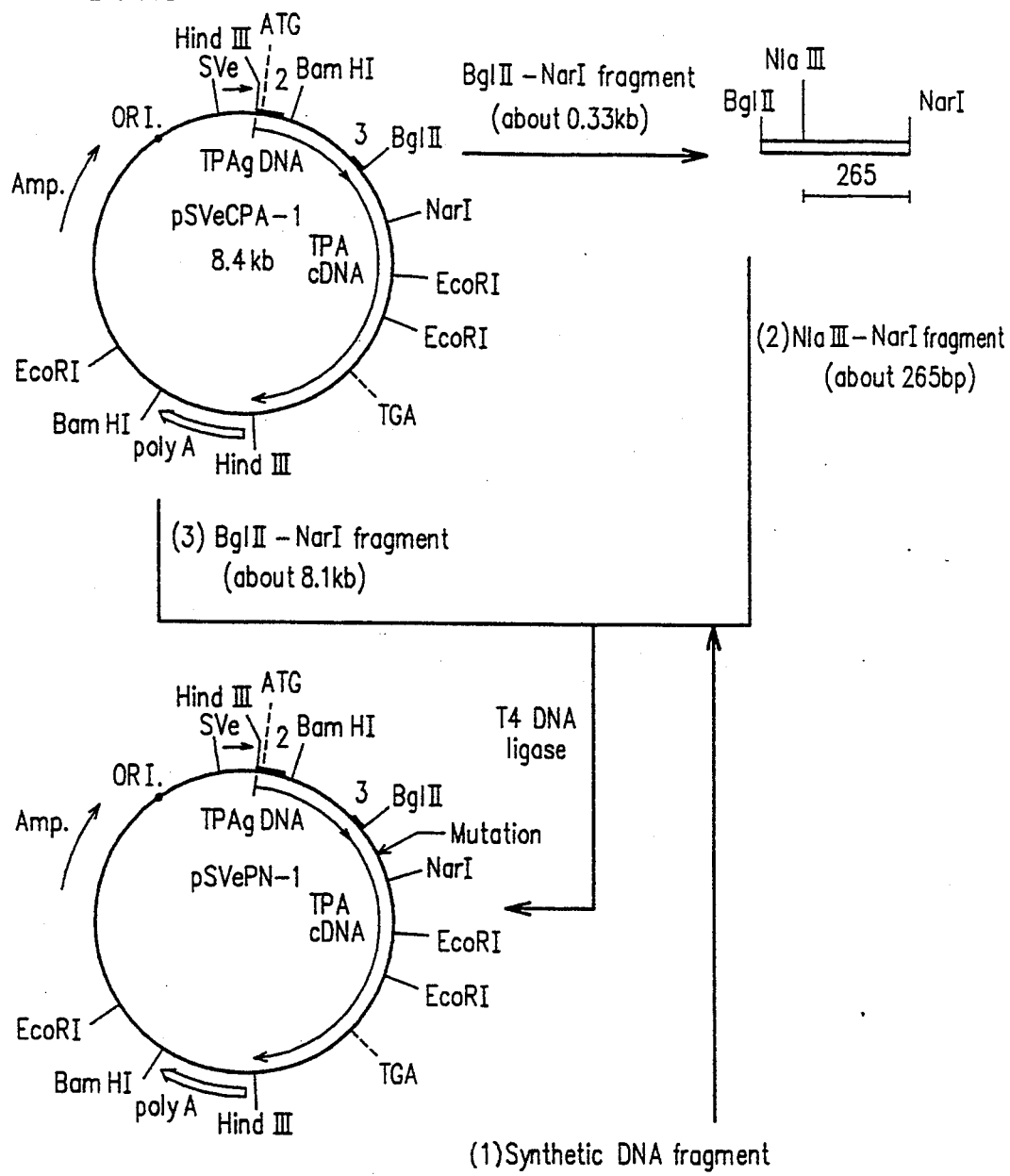
FIG. 2 is a schematic diagram showing the construction of the vector pSVePN1 which is one of the expression vectors of the present invention. Synthetic DNA fragments (SEQ ID Nos.: 1 and 2) are indicated.
Figure 3:
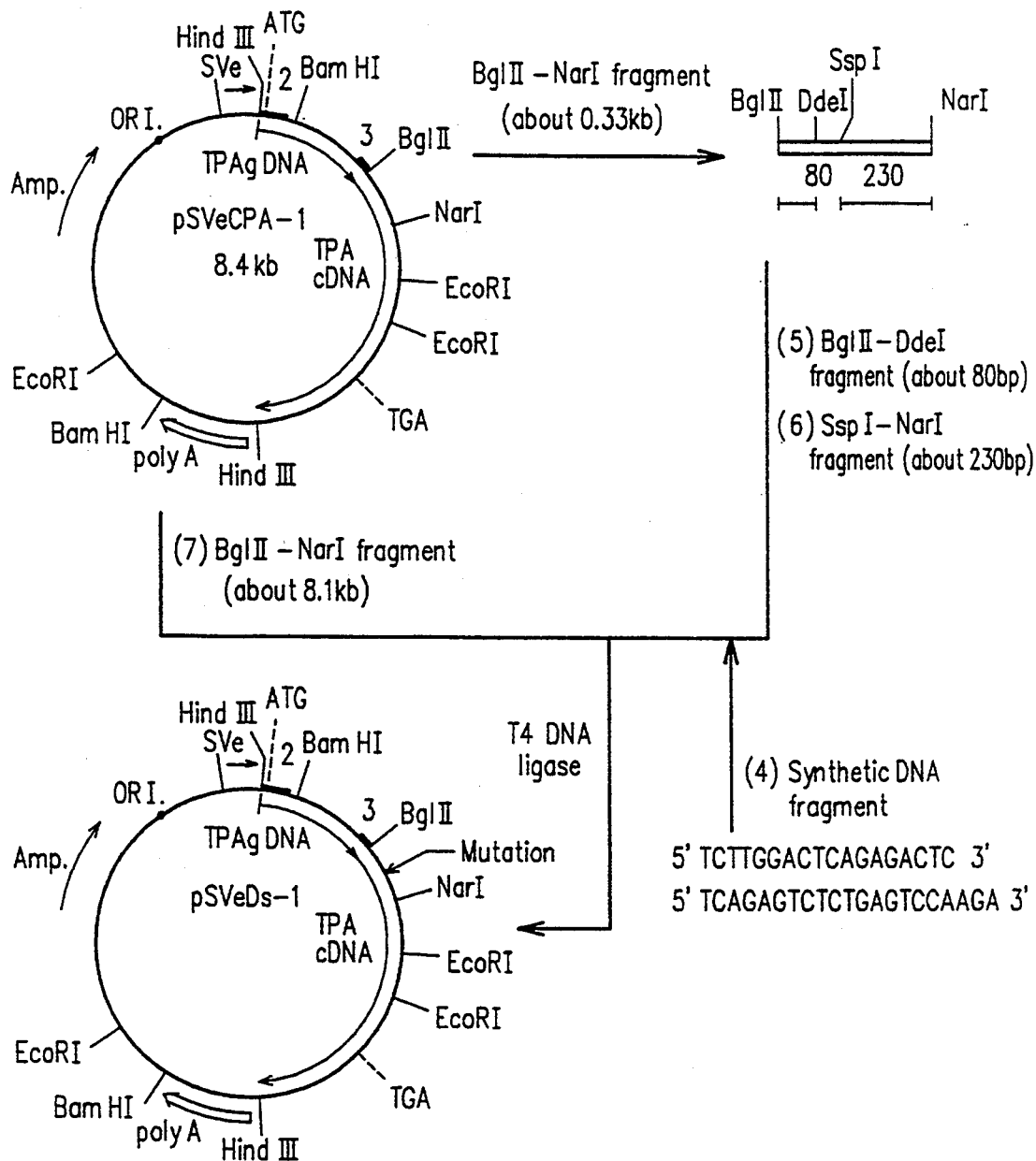
FIG. 3 is a schematic diagram showing the construction of the vector pSVeDS1 which is one of the expression vectors of the present invention. Synthetic DNA fragments (SEQ ID Nos.: 7 and 8) are shown.
Figure 4:
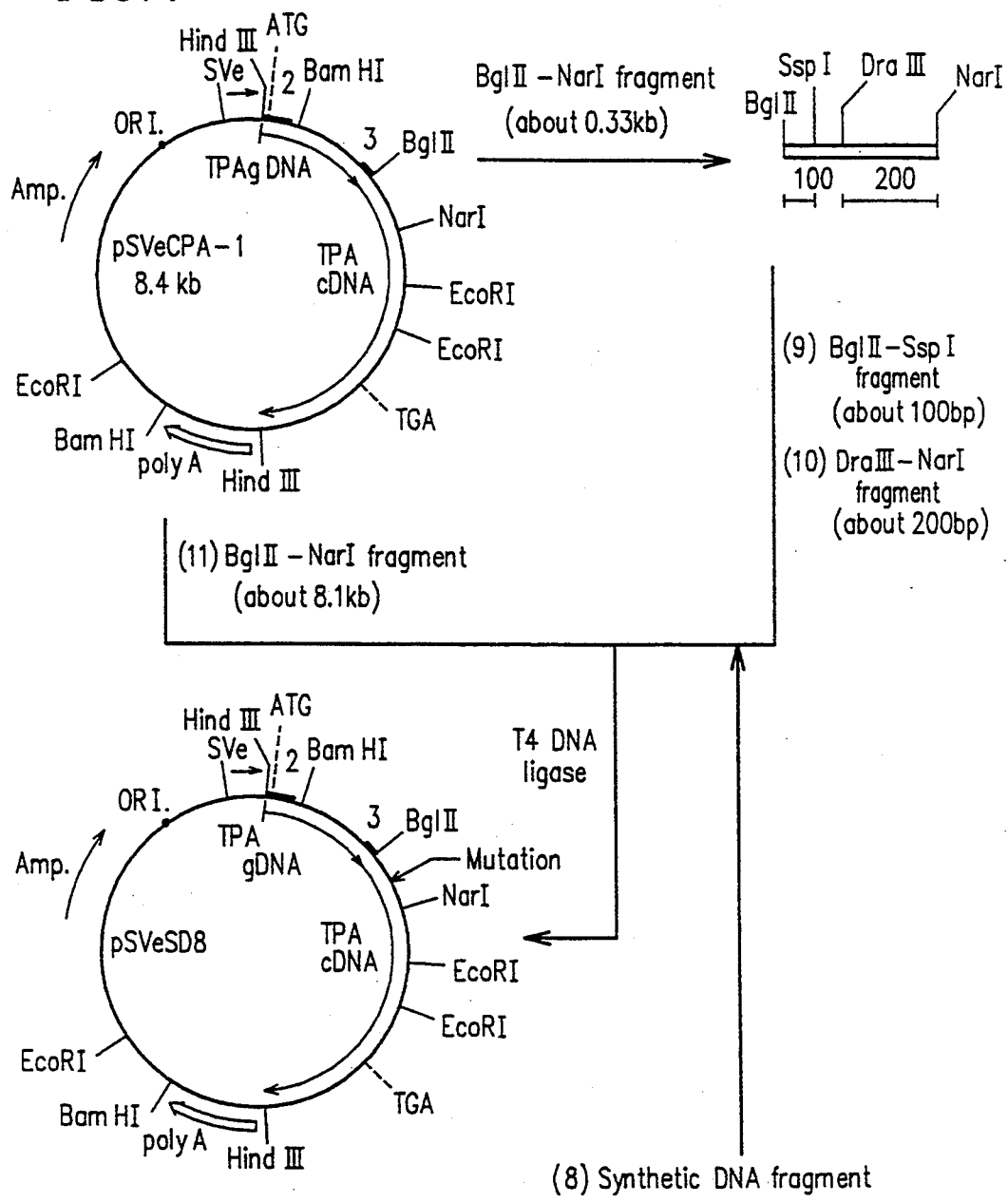
FIG. 4 is a schematic diagram showing the construction of the vector pSVeSD8 which is one of the expression vectors of the present invention. Synthetic DNA fragments (SEQ ID Nos.: 23 and 24) are indicated.

In the following account, the present invention will be described in accordance with the order of the processes employed for the production of VPAs of the present invention.

(I) Preparation of a DNA Sequence Encoding TPA

In order to modify the finger region and/or kringle region of TPA by genetic engineering techniques and thereby create VPAs with longer half-life in vivo, a DNA sequence encoding the amino acid sequence of TPA is required. Such a DNA sequence can be obtained by cloning cDNA or genomic DNA (hereinafter, genomic DNA is referred to as gDNA), or by chemical synthesis of DNA on the basis of the appropriate cDNA, gDNA, or TPA amino acid sequences.

cDNA encoding TPA has already been isolated by [Pennica, D. et al. (Nature, 301, 214 (1983), supra], while gDNA encoding TPA has been isolated by Ny, T. et al. [Proc. Natl. Acad. Sci. USA, 81, 5355 (1984)]; Brown, M. J. et al. [Gene, 33, 279 (1985)]; and Degen, S. J. F. et al. [J. Biol. Chem., 261, 6972 (1986)]. In the specification, the numbering of amino acid and cDNA sequences of TPA is in accordance with that of Pennica, D. et al. (supra), while the numbering of exons follows that of Ny, T. et al. (supra).

In addition, various TPA expression vectors obtained by gene manipulation are known, and, for example, a DNA sequence can be obtained by utilizing the TPA expression vector pSVePA-1 described in Japanese Laid-Open Patent Publication No. 62-14783. An example of the construction of an expression vector for a VPA of the present invention is as follows.

First, mRNA is isolated from a host containing the aforesaid expression vector pSVePA-1, for example, CHO-K1 cells transformed by this vector (Japanese Laid-Open Patent Publication No. 62-14783, supra). Then, cDNA is synthesized from this mRNA, a cDNA library is constructed, and cloning is performed. Cloning can be performed, for example, by plaque hybridization, using as a probe, a DNA fragment (encoding TPA) obtained by cleavage of the aforesaid expression vector with an appropriate restriction enzyme. In this manner, the clone CH79 which displays positive hybridization with this probe can be selected. When the DNA in this clone CH79 is isolated and the DNA sequence is analyzed by the Southern hybridization method, it is found that this clone contains a DNA fragment which hybridizes with the aforesaid probe and which can be cleaved to approximately 2.2 kb by HindIII. The cDNA clone pCH79 is then obtained by inserting this HindIII-cleaved fragment into a plasmid vector pUC19. Determination of the base sequence of the cDNA portion of this clone pCH79 by the M13 method reveals that the 5' terminus of this cDNA portion is linked with a HindIII recognition site originating from the plasmid vector pUC19, while approximately 150 bp downstream from this a BglII recognition site is present, and the stop codon TGA is located approximately 1500 bp further downstream. About 410 bp downstream from this TGA codon, an another HindIII recognition site originating from the plasmid vector pUC19 is present. Except for the substitution of thymine for cytosine at the 585th position and cytosine for adenine at the 1725th position, the base sequence of this cDNA portion is identical with that of the base sequence of TPA as reported by Pennica D. et al. (Nature, 301, 214, supra).

Using the cDNA sequence encoding TPA obtained in this manner, the TPA expression vectors which are essential for the preparation of the VPAs can be constructed.

(II) Construction of Expression Vectors

The construction of TPA expression vector pSVeC-PA-1 and VPA expression vectors is described as follows.

(II-A) Construction of TPA expression vector pSVeCPA-1

A TPA expression vector pSVeCPA-1 can be constructed by using the plasmid vector pSVeSal I (Japanese Laid-Open Patent Publication No. 62-14783, supra), the gDNA contained in the aforesaid vector pSVePA-1, and the cDNA of the aforesaid TPA. Specifically, the TPA expression vector pSVeCPA-1 is constructed by ligating the following three DNA fragments 1, 2, and 3. The construction of this expression vector is schematically shown in FIG. 1.

(1) HindIII-HindIII fragment of pSVeSal I

The plasmid vector pSVeSal I (Japanese Laid-Open Patent Publication No. 62-14783, supra) is cleaved with a restriction enzyme NcoI, the larger fragment (NcoI-NcoI fragment, approximately 4.7 kb) is isolated, and circularized with T4 DNA ligase. The plasmid vector pSVeSal I-HindIII so obtained is cleaved with HindIII, and the larger of the resulting DNA fragments (approximately 4.7 kb) is recovered.

(2) HindIII-BglII fragment of pSVePA-1

The TPA expression vector pSVePA-1 constructed by the use of the aforesaid gDNA is cleaved with HindIII and BglII, and the smaller of the resulting DNA fragments (approximately 1.9 kb) is recovered.

(3) BglII-HindIII fragment of pCH79

This DNA fragment (approximately 2 kb), containing cDNA of TPA, is obtained by cleavage of the aforesaid cDNA clone pCH79 with BglII and HindIII.

The TPA expression vector pSVeCPA-1 constructed in this manner is designed so that the early promoter of the SV40 virus is present upstream from the TPA gene in a position and direction permitting expression of the TPA gene, and TPA can be produced when the vector is introduced into mammalian cells. Not only the SV40 promoter but in fact any promoter which permits the expression of the TPA gene can be used for this purpose.

(II-B) Construction of an expression vector for VPA with a modified finger region Methods of preparing an amino acid-substituted VPA, with certain amino acid residues in the finger region replaced by different amino acids, include the following.

(1) Using a synthetic DNA primer to introduce mutations into a DNA sequence encoding the amino acid sequence of TPA.

(2) Introducing mutations in cassette form by direct use of synthetic DNA.

If the above method 2 is applied to cDNA of TPA, the synthesized DNA sequence may be either the entire cDNA or merely an appropriate portion (i.e., the portion into which mutations are introduced). If only a portion is synthesized, then, by using a suitable enzyme (i.e., restriction enzyme and T4 DNA ligase), a portion of the original cDNA sequence can be replaced by the synthetic DNA. For example, the following twelve varieties of VPAs with amino acid replacements to be described below, i.e., PN1, PN2, PN3, DS1, SD1, SD2, SD3, SD4, SD5, SD6, SD7, SD8, SD9 and SD10, can be produced by synthesizing DNA sequences encoding portions of an amino acid sequence including the amino acid replacements and constructing expression vectors containing the cDNA sequence of TPA with the corresponding portions replaced by the said synthetic DNA sequences.

PN1: a VPA in which arginine at the 7th position, aspartic acid at the 8th position, and gultamic acid at the 9th position from the N-terminus of the amino acid sequence of TPA are replaced by lysines, respectively.

PN2: a VPA in which lysine at the 10th position, threonine at the 11th position, glutamine at the 12th position, methionine at the 13th position, and isoleucine at the 14th position from the N-terminus of the amino acid sequence of TPA are replaced by glutamic acid, valine, serine, serine, and serine, respectively.

PN3: a VPA in which tyrosine at the 15th position, glutamine at the 16th position, glutamine at the 17th position, hisfidine at the 18th position, and glutamine at the 19th position from the N-terminus of the amino acid sequence of tissue plaminogen activator are replaced by phenylalanine, serine, serine, glutamic acid, and serine, respectively.

DS1: a VPA in which serine at the 28th position, asparagine at the 29th position, arginine at the 30th position, valine at the 31st position, and glutamic acid at the 32nd position, and tyrosine at the 32nd position from the N-terminus of the amino acid sequence of TPA are replaced by valine, serine, glutamic acid, serine, lysine, and asparginine, respectively.

SD1: a VPA in which asparagine at the 37th position, serine at the 38th position, glycine at the 39th position, argininen at the 40th position alanine at the 41st position and glutamine at the 42nd position from the N-terminus of the amino acid sequence of TPA are replaced by serine, valine, valine, gulutamic acid, serine, and serine, respectively.

SD2: a VPA in which asparagine at the 37th position, serine at the 38th position, glycine at the 39th position, argininen at the 40th position alanine at the 41st position and glutamine at the 42nd position from the N-terminus of the amino acid sequence of TPA are replaced by leucine, valine, valine, isolencine, valine, and lencine, respectively.

SD3: a VPA in which asparagine at the 37th position, serine at the 38th position, glycine at the 39th position, argininen at the 40th position alanine at the 41st position and glutamine at the 42nd position from the N-terminus of the amino acid sequence of TPA are replaced by serine, valine, valine, isolencine, serine, and serine, respectively.

SD4: a VPA in which asparagine at the 37th position, serine at the 38th position, glycine at the 39th position, argininen at the 40th position alanine at the 41st position and glutamine at the 42nd position from the N-terminus of the amino acid sequence of TPA are replaced by serine, valine, valine, isolenciene, valine, and serine, respectively.

SD5: a VPA in which asparagine at the 37th position, serine at the 38th position, glycine at the 39th position, argininen at the 40th position alanine at the 41st position and glutamine at the 42nd position from the N-terminus of the amino acid sequence of TPA are replaced by serine, valine, valine, isolencine, valine, and leucine, respectively.

SD6: a VPA in which asparagine at the 37th position, serine at the 38th position, glycine at the 39th position, argininen at the 40th position alanine at the 41st position and glutamine at the 42nd position from the N-terminus of the amino acid sequence of TPA are replaced by phenylalanine, leucine, phenylalanine, valine, leucine, and phenylalanine, respectively.

SD7: a VPA in which asparagine at the 37th position, serine at the 38th position, glycine at the 39th position, argininen at the 40th position alanine at the 41st position and glutamine at the 42nd position from the N-terminus of the amino acid sequence of TPA are replaced by valine, phenylalanine, leucine, phenylalanine, isoleucine, and valine, respectively.

SD8: a VPA in which asparagine at the 37th position, serine at the 38th position, glycine at the 39th position, argininen at the 40th position alanine at the 41st position and glutamine at the 42nd position from the N-terminus of the amino acid sequence of TPA are replaced by serine, valine, valine, glutamic acid, phenylalanine, serine, respectively.

SD9: a VPA in which asparagine at the 37th position, serine at the 38th position, glycine at the 39th position, arginine at the 40th position, and alanine at the 41st position form the N-terminus of TPA are replaced by serine, valine, valine, glutamic acid, and phenylalanine, respectively.

SD10: a VPA in which asparagine at the 37th position, serine at the 38th position, glycine at the 39th position, arginine at the 40th position, and alanine at the 41st position from the N-terminus of TPA are replaced by serine, valine, valine, glutamic acid, and serine, respectively.

The expression vectors pSVePN1, pSVePN2 and pSVePN3 used for the production of the aforesaid VPAs PN1, PN2 and PN3, respectively, can be constructed by ligating the following three types of DNA fragments 1, 2, and 3 by the use T4 DNA ligase. The construction of these expression vectors is schematically illustrated in FIG. 2, employing pSVePN1 as a typical example.

(1) Synthetic DNA fragments

Single-stranded synthetic DNA fragments with the following DNA sequences, two varieties for each vector, are synthesized. The two varieties of single-stranded DNA for each vector are complementary, and prior to the construction of the expression vector are annealed by a conventional method for use in the form of double-stranded DNA.

Synthetic DNA fragments (SEQ.ID NOS: 1 and 2) for construction of pSVePN1

5' GATCTTACCAAGTGATCTGCAAGAAGAAGAAAACGCAGATGATATACCAGCAACATCAGTCATG '3
5' ACTGATGTTGCTGGTATATCATCTGCGTTTTCTTCTTCTTGCAGATCACTTGGTAA 3'

Synthetic DNA fragments (SEQ ID NOS: 3 and 4) for construction of pSVePN2

5' GATCTTACCAAGTGATCTGCAGAGATGAAGAGGTCTCCTCCTCCTACCAGCAACATCAGTCATG 3'
5' ACTGATGTTGCTGGTAGGAGGAGGAGACCTCTTCATCTCTGCAGATCACTTGGTAA 3'

Synthetic DNA fragments (SEQ ID NOS: 5 and 6) for construction of pSVePN3

5' GATCTTACCAAGTGATCTGCAGAGATGAAAAACGCAGATGATATTCTCCTCTGAGTCCTCATG 3'
5' AGGACTCAGAGGAGAATATCATCTGCGTTTTTCATCTCTGCAGATCACTTGGTAA 3'

(2) NlaIII-NarI fragment of pSVeCPA-1

The smaller of the DNA fragments (approximately 0.33 kb) obtained by digestion with BglII and NarI of the TPA expression vector pSVeCPA-1 constructed as in item II-A above, is digested with NlaIII, which cleaves the base sequence of the cDNA encoding TPA in the vicinity of the 250th base pair, thus obtaining a DNA fragment of approximately 265 bp.

(3) BglII-NarI fragment of pSVeCPA-1

This is the larger of the DNA fragments (approximately 8.1 kb) obtained by digestion with BglII and NarI of the TPA expression vector pSVeCPA-1 constructed as shown in item II-A above.

Expression vectors pSVePN1, pSVePN2 and pSVePN3 for the three VPAs PN1, PN2, and PN3, respectively, are constructed by ligation of the DNA fragments 1, 2, and 3. The expression vectors are introduced into *E. coli* DH1 (ATCC 33849), respectively, resulting in transformants.

The expression vector pSVeDS1 used for the production of the aforesaid VPA DS1 can be constructed by ligating the following four types of DNA fragments 4, 5, 6, and 7, with the use of T4 DNA ligase. The construction of this expression vector is schematically shown in FIG. 3.

(4) Synthetic DNA fragments

Two single-stranded synthetic DNA fragments (SEQ ID Nos. 7 and 8) with the following DNA sequences are synthesized. These two varieties of single-stranded DNA are complementary, and prior to the construction of the expression vector are annealed by a conventional method for use in the form of double-stranded DNA.

Synthetic DNA fragments (SEQ ID NOS: 7 and 8) for construction of pSVeDS1:

5' TCTTGGACTCAGAGACTC 3'
5' TCAGAGTCTCTGAGTCCAAGA 3'

(5) BglII-DdeI fragment of pSVeCPA-1

The smaller of the DNA fragments (approximately 0.33 kb) obtained by digestion with BglII and NarI of the TPA expression vector pSVeCPA-1 constructed as in item II-A above, is digested with DdeI, which cleaves the cDNA sequence encoding TPA in the vicinity of the 270th base pair, thus obtaining a DNA fragment of approximately 80 bp.

(6) SspI-NarI fragment of pSVeCPA-1

The BglII-NarI fragment (0.33 kb) obtained as in item 5 above is digested with SspI, which cleaves the base sequence of the cDNA encoding TPA in the vicinity of the 290th base pair, thus obtaining a DNA fragment of approximately 230 bp.

(7) BglII-NarI fragment of pSVeCPA-1

This is the larger of the DNA fragments (approximately 8.1 kb) obtained by digestion with BglII and NarI of the TPA expression vector pSVeCPA-1 constructed as in item II-A above.

Expression vector pSVeDS1 for the VPA DS1 is constructed by ligating the DNA fragments 4, 5, 6, and 7. The expression vector is introduced into *E. coli* DH1 (ATCC 33849), resulting in a transformant.

FIG. 6 shows the amino acid sequences in the vicinity of the N-terminus of the VPAs PN1, PN2, PN3 and DS1 produced by the aforesaid expression vectors, in comparison with that of TPA.

The expression vectors pSVeSD1, pSVeSD2, pSVeSD3, pSVeSD4, pSVeSD5, pSVeSD6, pSVeSD7, pSVeSD8, pSVeSD9 and pSVeSD10 used for the production of the aforesaid VPAs SD1, SD2, SD3, SD4, SD5, SD6, SD7, SD8, SD9 and SD10, respectively, can be constructed by ligating the following four types of DNA fragments 8, 9, 10, and 11 by the use T4 DNA ligase. The construction of these expression vectors is schematically illustrated in FIG. 4, employing pSVeSD8 as a typical example.

(8) Synthetic DNA fragments

Single-stranded synthetic DNA fragments with the following DNA sequences, two varieties for each vector, are synthesized. The two varieties of single-stranded DNA for each vector are complementary, and prior to the construction of the expression vector are annealed by a conventional method for use in the form of double-stranded DNA.

Synthetic DNA fragments (SEQ ID NOS: 9 and 10) for construction of pSVeSD1

5' GTGGCAGGAGGACTCCACCACAGAGCACCAGCAAT 3'
5' ATTGCTGGTGCTCTGTGGTGGAGTCCTCCTGCCACTCA 3'

Synthetic DNA fragments (SEQ ID NOS: 11 and 12) for construction of pSVeSD2

5' GTGGCACAGCACAATCACCACCAGGCACCAGCAGT 3'
5' ACTGCTGGTGCCTGGTGGTGATTGTGCTGTGCCACTCA 3'

Synthetic DNA fragments (SEQ ID NOS: 13 and 14) for construction of pSVeSD3

5' GTGGCAGGAGGAGATCACCACAGAGCACCAGCAGT 3'
5' ACTGCTGGTGCTCTGTGGTGATCTCCTCCTGCCACTCA 3'

Synthetic DNA fragments (SEQ ID NOS: 15 and 16) for construction of pSVeSD4

5' GTGGCAGGAGACAATCACCACAGAGCACCAGCAGT 3'
5' ACTGCTGGTGCTCTGTGGTGATTGTCTCCTGCCACTCA 3'

Synthetic DNA fragments (SEQ ID NOS: 17 and 18) for construction of pSVeSD5

5' GTGGCACAGCACAATCACCACAGAGCACCAGCAGT 3'
5' ACTGCTGGTGCTCTGTGGTGATTGTGCTGTGCCACTCA 3'

Synthetic DNA fragments (SEQ ID NOS: 19 and 20) for construction of pSVeSD6

5' GTGGCAGAACAGCACAAACAGGAAGCACCAGCAGT 3'
5' ACTGCTGGTGCTTCCTGTTTGTGCTGTTCTGCCACTCA 3'

Synthetic DNA fragments (SEQ ID NOS: 21 and 22) for construction of pSVeSD7

5' GTGGCAGACAATGAACAGGAAGACACACCAGCAGT 3'
5' ACTGCTGGTGTGTCTTCCTGTTCATTGTCTGCCACTCA 3'

Synthetic DNA fragments (SEQ ID NOS: 23 and 24) for construction of pSVeSD8

5' GTGGCAGGAAAACTCCACCACAGAGCACCAGCAAT 3'
5' ATTGCTGGTGCTCTGTGGTGGAGTTTTCCTGCCACTCA 3'

Synthetic DNA fragments (SEQ ID NOS: 25 and 26) for construction of pSVeSD9

-continued
5' GTGGCACTGAAACTCCACCACAGAGCACCAGCAGT 3'
5' ACTGCTGGTGCTCTGTGGTGGAGTTTCAGTGCCACTCA 3'

Synthetic DNA fragments (SEQ ID NOS: 27 and 28) for construction of pSVeSD10

5' GTGGCATTGGGATTCCACCACAGAGCACCAGCAGT 3'
5' ACTGCTGGTGCTCTGTGGTGGAATCCCAATGCCACTCA 3'

(9) BglII-SspI fragment of pSVeCPA-1

The smaller of the DNA fragments (approximately 0.33 kb) obtained by digestion with BglII and NarI of the TPA expression vector pSVeCPA-1 constructed as in item II-A above, is digested with SspI, which cleaves the cDNA sequence encoding TPA in the vicinity of the 290th base pair, thus obtaining a DNA fragment of approximately 100 bp.

(10) DraIII-NarI fragment of pSVeCPA-1

The BglII-NarI fragment (0.33 kb) obtained in item (9) above is digested with DraIII, which cleaves the base sequence of the cDNA encoding TPA in the vicinity of the 320th base pair, thus obtaining a DNA fragment of approximately 200 bp.

(11) BglII-NarI fragment of pSVeCPA-1

This is the larger of the DNA fragments (approximately 8.1 kb) obtained by digestion with BglII and NarI of the TPA expression vector pSVeCPA-1 constructed in item II-A above.

Expression vectors pSVeSD1, pSVeSD2, pSVeSD3, pSVeSD4, pSVeSD5, pSVeSD6, pSVeSD7, pSVeSD8, pSVeSD9, and pSVeSD10 are constructed by ligating DNA fragments 8, 9, 10, and 11, respectively. The expression vectors are introduced into *E. coli* DH1 (ATCC 33849), respectively, resulting in transformants.

(II-C) Construction of expression vectors for VPAs with modified kringle regions Expression vectors for VPAs; formed by replacement of certain amino acid residues in the kringle 1 region of TPA by other amino acids are prepared, for example, by the method using synthetic DNA primers to introduce mutations into the DNA sequence encoding the amino acid sequence of TPA (i.e., site-directed mutagenesis).

For example, using this site-directed mutagenesis technique, the following two VPAs; KM4 and KM21 in which amino acid replacements have been introduced can be produced.

KM4: a VPA in which glycine at the 161st position, lysine at the 162nd position, and serine at the 165th position from the N-terminus of the amino acid sequence of TPA are replaced by arginine, arginine, and tryptophan, respectively.

KM21: a VPA in which asparagine at the 115th position from the N-terminus of the amino acid sequence of TPA is replaced by proline.

The aforesaid VPAs with modified kringle regions can be prepared, for example, by excising a DNA fragment encoding a portion of the amino acid sequence of TPA (containing a site of the amino acid to be replaced) from a TPA expression vector, for example, pSVeCPA-1 obtained as in item II-A, and incorporating this fragment into a single-stranded phage or plasmid such as M13 or pUC119 suitable for introduction into an *E. coli* host. For example, the smaller of the fragments obtained by cleavage of pSVeCPA-1 with NarI and SmaI is inserted into M13mp11 (manufactured by Takara Shuzo, Co., Ltd.) which has likewise been treated with NarI and SmaI, thereby obtaining a recombinant phage vector M13NS. Next, a portion of a DNA fragment homologous to the aforesaid excised DNA fragment (containing a portion into which the mutations are to be introduced, and the bases present in the portion has been replaced by desired bases) is synthesized separately for use as a primer. For example, in order to obtain expression vector pSCKM4 for production of KM4, the following DNA fragment I (SEQ ID No. 24) is synthesized.

5'
   TGCTGCAGAACTCCCAGCT-
   GTACCTCCTCGCCTTAAAGACG 3'   (I)

Similarly, in order to obtain an expression vector pSCKM21 for production of KM21, the following DNA fragment II (SEQ ID No. 30) is synthesized.

5' GCTGTTCCAGGGGGTGCACTCG 3'   (II)

This primer, e.g., the aforesaid DNA fragment I, is phosphorylated with T4 polynucleotide kinase, then annealed to the aforesaid recombinant single-stranded phage or plasmid, and the DNA chain is extended by the conventional method. This procedure may be accomplished by the use of a commercially available in vitro mutageneric system kit. The plasmid so obtained (M13-NSM4), containing the mutant portion, is then introduced into a suitable host, for example, *E. coli* JM109, and amplified. Next, this plasmid M13-NSM4 is treated with NarI and SmaI, the smaller fragment (approximately 1.2 kb; corresponding to the portion of the TPA-coding DNA containing the mutation) is isolated, and is ligated to the aforesaid NarI-SmaI fragment of pSVeCPA-1 (larger fragment, approximately 7 kb), thereby obtaining an expression vector (pSCKM4) for production of KM41. Similarly, using the DNA fragment II, an expression vector (pSCKM21) for producing KM21 is constructed.

Transformants are obtained by introducing each of the two expression vectors pSCKM4 and pSCKM21 constructed in this manner into *E. coli* DH1 (ATCC 33849).

(II-D) Construction of expression vectors for VPAs with modifications of both finger region and kringle region Expression vectors for finger-kringle 1 modified VPAs, with amino acid replacements in both the finger region and the kringle 1 region, can be prepared by combining an expression vector for TPA with a modified finger region, prepared as in the above item II-B, and an expression vector for TPA with a modified kringle region, prepared as in the above item II-C, thereby constructing a new expression vector. For example, the two types of VPAs KS48, and KS218, to be described below, can be produced by this method.

KS48: a VPA in which asparagine at the 37th position, serine at the 38th position, glycine at the 39th position, arginine at the 40th position, alanine at the 41st position, glutamine at the 42nd position, glycine at the 161st position, lysine at the 162nd position, and serine at the 165th position from the N-terminus of the amino acid sequence of TPA are replaced by serine, valine, valine, glutamic acid, phenylalanine, serine, arginine, arginine, and tryptophan, respectively.

KS218: a VPA in which asparagine at the 37th position, serine at the 38th position, glycine at the 39th position, arginine at the 40th position, alanine at the 41st position, glutamine at the 42nd position and asparagine at the 115th position from the N-terminus of the amino acid sequence of TPA are replaced by serine, valine, valine, glutamic acid, phenylalanine, serine, and proline, respectively.

Figure 5:
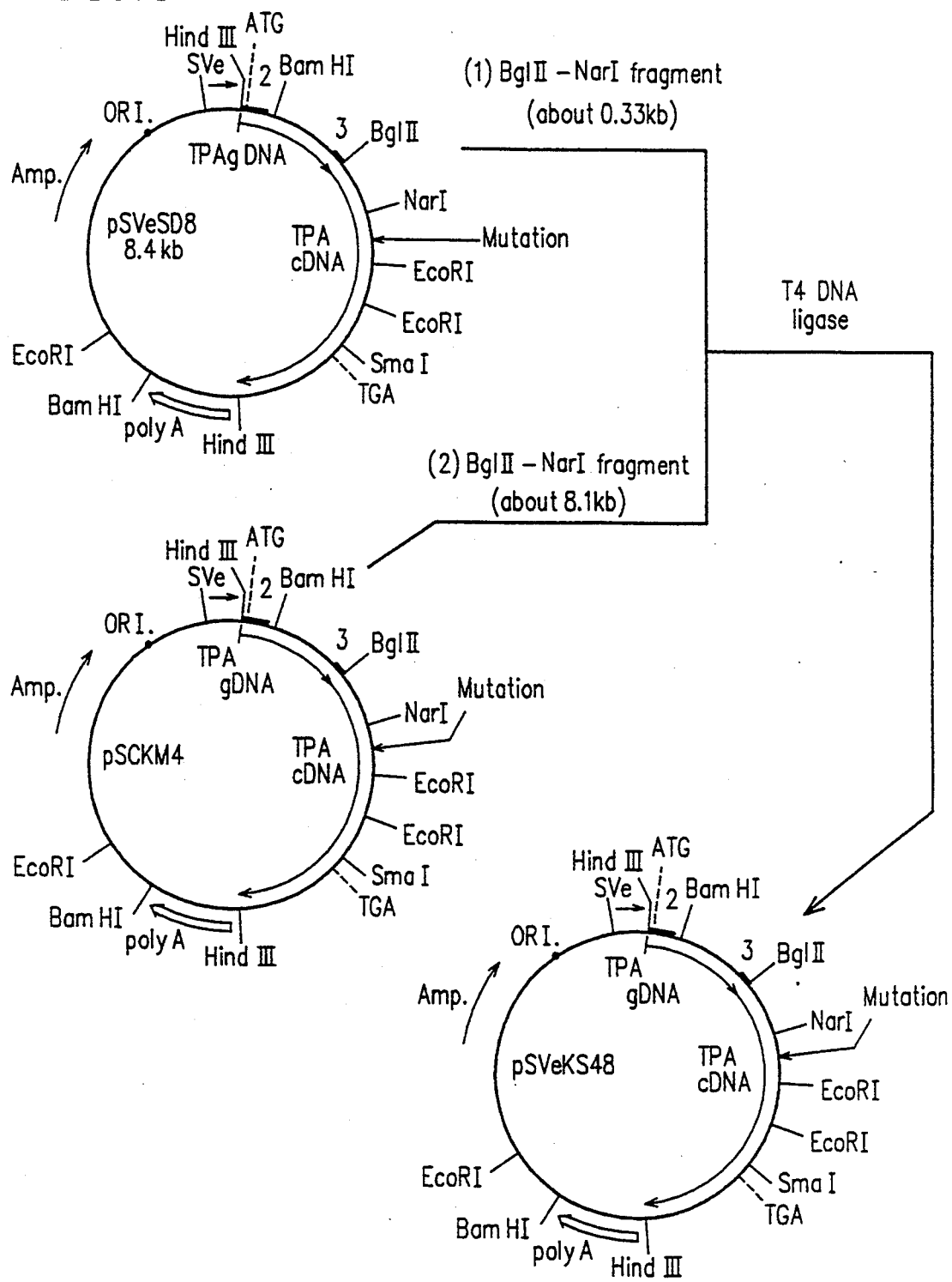
FIG. 5 is a schematic diagram showing the construction of the vector pSVeKS48 which is one of the expression vectors of the present invention.
Figure 6:
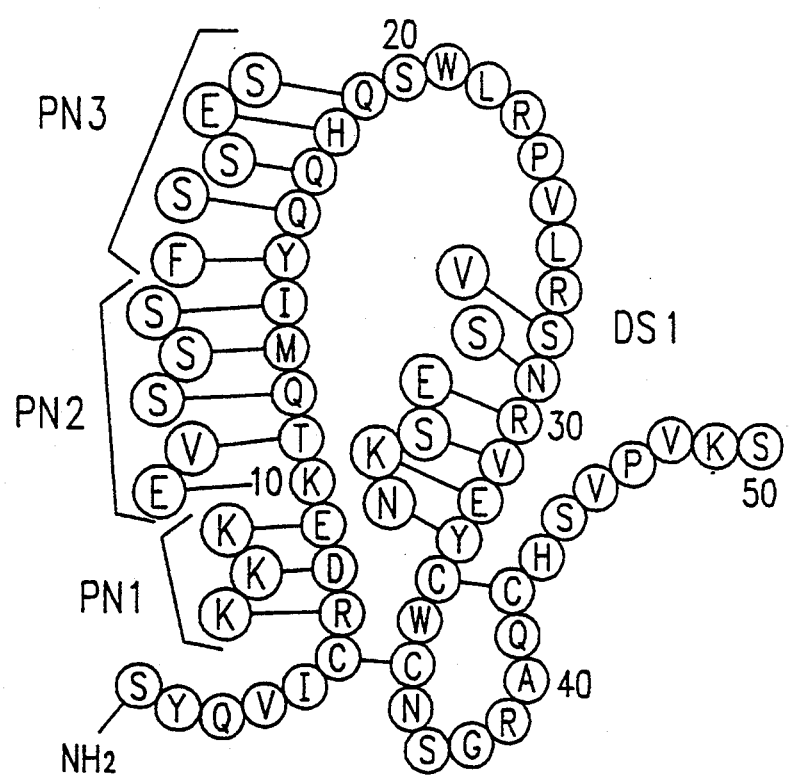
FIG. 6 is a schematic diagram showing the amino acid sequence of the finger region in the neighborhood of the N-terminus of TPA (SEQ ID No. 31) as well as the amino acid sequences of VPAs; PN1(SEQ ID No. 32), PN2 (SEQ ID No. 33), PN3 (SEQ ID No. 34) and DS1 (SEQ ID No. 35) in the finger region.

Expression vectors pSVeKS48 and pSVeKS218 for the production of these VPAs can be constructed by ligating the two types of fragments 1 and 2 indicated below. The construction of these expression vectors is schematically illustrated in FIG. 5, employing pSVeKS48 as a typical example.

(1) A smaller fragment (approximately 0.33 kb) obtained by digestion of the expression vector pSVeSD8 or pSVeSD4 for the finger region VPA with BglII and NarI, (2) A larger fragment (approximately 8.1 kb) obtained by digestion of the expression vector pSCKM4 or pSCKM21 for kringle region VPA with BglII and NarI.

Two VPA expression vectors pSVeKS48 and pSVeKS218 are obtained by ligating the DNA fragments of the above two varieties 1 and 2, respectively. The expression vectors are introduced into *E. coli* DH1 (ATCC 33849) respectively, resulting in transformants.

A transformant carrying the expression vector pSVeKS48 was designated *E. coli* DH1 KS48, and deposited with the Fermentation Research Institute, Agency of Industrial Science and Technology, 1-3, Higashi 1-chome, Tsukuba-shi, Ibaraki-ken, Japan, on Jun. 25, 1990, under Accession No. BP-3083, where it will be maintained under the terms of the Budapest Treaty.

(III) Marker Genes

Genes such as Ecogpt [Mulligaan, R. C., et al., Science, 209, 1422 (1980)], neo [Southern, P. J., et al., Journal of Molecular and Applied Genetics 1, 327 (1982)], and dhfr [Wigler, M., et al., Proc. Natl. Acad. Sci. USA, 77, 327 (1980)] can be used as markers for the selection of transformants obtained by the introduction of the aforesaid expression vectors into animal cells. These marker genes can be included in either the expression vectors for VPAs or in plasmids other than the said vectors. In the latter case, a plasmid vector possessing a selectable marker gene is constructed and used after mixing with the TPA expression vector in an appropriate proportion, thus permitsion vector in an appropriate proportion, thus permitting selection of the transformants. For example, a marker vector pSV2neo-dhfr possessing the neo and dhfr genes is suitable for this purpose, and can be constructed in the following manner. The rDNA vector pSV2dhfr (American Type Culture Collection, rDNA Vector 37146), possessing the dhfr gene, is cleaved with PvuII. The resulting PvuII-PvuII fragments are ligated BamHI linker-d (pCGGATCCG) using T4 DNA ligase, thereby obtaining a vector pSV2Bdhfr. This vector is cleaved with BamHI, and the resulting BamHI-BamHI fragment is ligated, using T4 DNA ligase, with a BamHI-BamHI fragment obtained by cleaving the rDNA vector pSV2neo (American Type Culture Collection, rDNA Vector 37149) with BamHI, thereby obtaining a circular marker vector pSV2neo-dhfr.

(IV) Transformation of Cultured Animal Cells and Production of VPAs

Cultured animal cells are used as hosts, and CH0-K1 (ATCC CCL-61) is particularly suitable. By the use of this type of cultured animal cells, the VPAs can be produced in glycosylated form.

Although the various methods used for the introduction of the aforesaid expression vectors into animal cells differ with respect to transfection efficiency, those applicable for the present purpose include the calcium phosphate method [Wigler, M., et al., Cell, 11, 233 (1977)], the microinjection method [Anderson, W. F., et al., Proc. Natl. Acad. Sci. USA, 77, 5399 (1989)], the liposome method, the DEAE-dextran method, the cell fusion method [Schoffner, W., et al., Proc. Natl. Acad. Sci. USA, 77, 2163 (1980)], and the electroporation method [Tatsuya, M., et al., Cell Technology, 6, 494 (1987)]. After the TPA expression vector has been introduced into the host cells by one of these methods, the transformants are selected according to the characters conferred by the marker gene mentioned in above item III.

By the measurement of the plasminogen-activating activity (i.e., the degree of activity of the plasminogen-activating effect) in the culture medium of the respective transformant cells, it can be determined if the transformants so obtained actually produce the desired VPAs. Techniques available for the measurement of plasminogen-activating activity include the utilization of fibrin plates containing plasminogen [Mackie, M., et al., British Journal of Haematology, 47, 77 (1981)], the measurement of decomposition of the synthetic substrate S-2251 on which plasmin acts [Allen, R. A., and Pepper, D. S., Thrombosis and Haemostasis, 45, 43 (1981)], the CLT method [Gaffney, P. T., and Cartis, A.D., Thrombosis and Haemostasis 53, 134 (1985)], and ELISA [Holvoest, T., et al., Thrombosis and Haemostasis, 54, 684 (1985)].

(V) Recovery and Purification of VPAs

Transformants producing the VPAs can be cultivated by any method appropriate for the animal cells used as hosts. Recovery and purification of the VPAs from the culture can be accomplished by a suitable combination of techniques such as column chromatography using an appropriate support (e.g., CPG-10, chelating Sepharose, Con-A Sepharose, ion-exchangers, Octyl Sepharose, Sephadex gel, etc.), antibody column chromatography, electrophoresis, etc. In experiments according to the present invention, 1-3 mg of purified VPAs were obtained from 2-6 liters of culture broth for each of cell strains producing the respective VPAs.

The plasminogen-activating activity of the purified VPAs obtained in this manner can be measured by the above-mentioned methods, while affinity for fibrin can be assessed by the method of Collen, D. et al. [Blood, 71, 216 (1988)], using uptake by a fibrin clot as an index. In vitro fibrolytic ability can be measured by the method of Larsen, G. R. et al. [J. Biol. Chem., 263, 1023 (1988)], using release of radioactivity from $^{125}$I-fibrin; or by the method of Collen, D. et al. [Thromb. Haemost., 52, 308 (1984)]. Fibrin dependence of TPA activity or plasminogen-activating activity can be assessed by the method of Collen, D. et al., using the synthetic substrate S-2251 on which plasmin acts [J. Biol. Chem., 257, 2912 (1982), sapra] or by the method of Takada, A. et al. [Haemostasis, 18, 117 (1988)]. Persistence in the blood can be evaluated as half-life using the method described by Beebe, D. P. et al. [Thrombosis Research, 43, 663 (1986)] or by Mattson, Ch. et al. [Thrombosis Research, 30, 91 (1983)].

Various properties relating to dissolution of thrombi include specific activity, affinity for fibrin, dependence of activity on fibrin, resistance to protease, persistence in the blood, plasminogen-activating activity, in vitro thrombolytic activity, sensitivity to inhibitors, etc. The VPAs of the present invention possess thrombolytic characteristics of nearly the same level as those of TPA, and moreover, display excellent persistence in the blood. These characteristics will be further clarified in the following examples.

EXAMPLES

The present invention will now be explained in further detail with reference to specific examples.

All experiments in connection with the present invention were performed in accordance with the "Guidelines for Recombinant DNA Experiments" stipulated under the authority of the Prime Minister of Japan. Also, the following learned journals and treatises were used for reference with regard to the detailed procedures adopted in the management and use of phages, plasmids, DNA, various enzymes, E. coli and other materials employed in the examples and comparative examples.

1. Protein, nucleic acid, and enzyme, 26 (4), (1981), special issue, Genetic Engineering, Kyoritsu Shuppan (Japan).
2. Experimental Method for Genetic Engineering, written and ed. by Takagi, Y. (1980), Kodansha (Japan).
3. Manual for Genetic engineering, written and ed. by Takagi, Y. (1982), Kodansha (Japan).
4. Molecular cloning, a Laboratory Manual, T. Maniatis et al., ed., (1982), Cold Spring Harbor Laboratory.
5. Methods in Enzymology, L. Grossmam et al., ed., 65 (1980), Academic Press.
6. Methods in Enzymology, R. Wu, ed., 65 (1979), Academic Press.

Example 1

(I) Preparation of DNA fragment encoding TPA

A DNA fragment encoding TPA was prepared from cDNA in the following manner.

First, using the guanidine-hot phenol method, total RNA was extracted from CHO-K1 cells which had been transformed with a TPA expression vector pSVePA-1, which utilizes genomic DNA (gDNA) (Japanese Laid-Open Patent Publication No. 62-14783, supra). This total RNA extract was subjected to oligo-dT cellulose chromatography, and the polyA+mRNA fraction so obtained was subjected to molecular weight fractionation by the sucrose gradient centrifugation method, thereby obtaining a fraction containing mRNA of TPA. Using this mRNA fraction, cDNA was prepared with a commercial cDNA synthesis kit Amersham, and this was used for preparing a cDNA library. A commercial cDNA cloning kit (Amersham) employing lambda-gt10 was used for preparing this cDNA library. Next, this library was subjected to plaque hybridization by the conventional method. Using, as a probe, an approximately 2.5 kb DNA fragment containing the 10th, 11th and 12th exons, obtained by cleavage of the aforesaid expression vector pSVePA-1 with an restriction enzyme XbaI, the phage clones which displayed positive hybridization with the said DNA fragment were selected.

DNA was isolated from each of the several positive phage clones obtained in this manner, and after digestion with a restriction enzyme HindIII (Takara Shuzo, Co., Ltd.), the DNA was subjected to agarose gel electrophoresis. Then, the positive phage clones were analyzed by Southern hybridization, using as a probe, the same XbaI-cleaved 2.5 kb DNA fragment which was employed in the aforesaid plaque hybridization procedure. The results showed that a clone designated as CH79 hybridized with the aforesaid probe, and contained a DNA fragment which was cleaved into an approximately 2.2 kb fragment by HindIII. This approximately 2.2 kb HindIII-cleaved DNA fragment was isolated by agarose gel electrophoresis, and using T4 DNA ligase, ligated to a plasmid vector pUC19 (Takara Shuzo, Co., Ltd.) which had likewise been digested with HindIII. The ligation product was then introduced into E. coli DH1, thus obtaining a cDNA clone pCH79. The base sequence of the cDNA portion of this clone was determined with a commercial sequencing kit (Takara Shuzo, Co., Ltd.) employing the M13 method. The results revealed that the 5' terminus of this cDNA portion was linked with a HindIII recognition site originating from the plasmid vector pUC19, while approximately 150 bp downstream from this portion, a BglII recognition site was present, and approximately 1500 bp further downstream the termination codon TGA was present. Approximately 410 bp downstream from this TGA codon, another HindIII recognition site derived from the plasmid vector pUC19 was present. The base sequence of this cDNA portion was identical with that reported by Pennica et al. (Nature, 301, 214, supra), except that the cytosine in the 585th position was replaced by thymine and the adenine in the 1725th position by cytosine.

(II) Construction of expression vectors

A TPA expression vector pSVeCPA-1 and expression vectors for VPAs were constructed as follows.

(II-A) Construction of TPA expression vector pSVeCPA-1

A TPA expression vector pSVeCPA-1 was constructed by the ligation of three DNA fragments obtained in the following items 1, 2, and 3. The construction of this expression vector is schematically shown in FIG. 1.

(1) HindIII-HindIII fragment derived from pSVeSalI

A plasmid vector pSVeSalI (Japanese Laid-Open Patent Publication No.62-14783, supra) was cleaved with a restriction enzyme NcoI, and the larger DNA fragment so obtained (NcoI-NcoI fragment, approximately 4.7 kb) was isolated. This DNA fragment contained an early promoter region (SVe) including an origin (Ori) for replication in E. coli, derived from SV40; a sequence containing a polyadenylation signal (polyA); an ampicillin-resistance gene (Amp.); and two HindIII recognition sites. This NcoI-NcoI fragment was circularized with T4 DNA ligase, and the plasmid vector so obtained, designated as pSVeSalI-HindIII, was amplified by introduction into E. coli DH1. Next, this plasmid vector pSVeSalI-HindIII was isolated from the E. coli DH1 by the conventional method, cleaved with HindIII, and the larger of the resulting fragments (HindIII-HindIII fragment, approximately 4.7 kb) was recovered.

(2) HindIII-BglII fragment of pSVePA-1

The aforesaid TPA expression vector pSVePA-1, constructed by utilizing gDNA, was cleaved with Hin dIII and BglII, thereby obtaining a small (approximately 1.9 kb) DNA fragment (HindIII-BglII fragment). This HindIII-BglII fragment contained the entire second exon and a portion of the third exon of gDNA encoding TPA.

(3) BglII-HindIII fragment of pCH79

First, pCH79, the cDNA clone obtained as in the above item I, was cleaved with BglII and HindIII, thereby obtaining a DNA fragment (BglII-HindIII fragment) of approximately 2 kb containing TPA cDNA.

A TPA expression vector, designated as pSVeC-PA-1, was then constructed by ligating the aforesaid DNA fragments 1, 2, and 3 with T4 DNA ligase. This vector pSVeCPA-1 was introduced into an E. coli DH1, and used in the construction of the following expression vectors for VPAs. This TPA expression vector pSVeC-PA-1 comprises a gene having the ability of producing TPA, and contains a portion derived from gDNA (from the second exon indicated by numeral 2 to the BglII recognition site of the third exon indicated by numeral 3 in FIG. 1) and a portion derived from cDNA.

(II-B) Construction of expression vectors for finger region VPA

The fourteen VPAs composed of the amino acid sequence of TPA with the respective amino acid replacements indicated in Table 1, 2, or 3 were designated by PN1, PN2, PN3, DS1, SD1, SD2, SD3, SD4, SD5, SD6, SD7, SD8, SD9, and SD10.

TPA secreted from cell lines transfected with pSVePA-1 containing TPA gene is refferes to as recombinant tPA, rTPA.

TABLE 1

| | Expression Vector | Amino acid number from N-terminus | | | | | | | | | | | | |
|---|---|---|---|---|---|---|---|---|---|---|---|---|---|---|
| | | 7 | 8 | 9 | 10 | 11 | 12 | 13 | 14 | 15 | 16 | 17 | 18 | 19 |
| TPA | pSVeCPA-1 (SEQ ID NO 31) | Arg | Asp | Glu | Lys | Tyr | Gln | Met | Ile | Tyr | Gln | Gln | His | Gln |
| VPAs | | | | | | | | | | | | | | |
| PN1 | pSVePN1 (SEQ ID NO 32) | Lys | Lys | Lys | — | — | — | — | — | — | — | — | — | — |
| PN2 | pSVePN2 (SEQ ID NO 33) | — | — | — | Glu | Val | Ser | Ser | Ser | — | — | — | — | — |
| PN3 | pSVePN3 (SEQ ID NO 34) | — | — | — | — | — | — | — | — | Phe | Ser | Ser | Glu | Ser | denote the same amino acid as that of TPA.

TABLE 2

| | Expression Vector | Amino acid number from N-terminus | | | | | |
|---|---|---|---|---|---|---|---|
| | | 28 | 29 | 30 | 31 | 32 | 33 |
| TPA | pSVeCPA-1 (SEQ ID NO 31) | Ser | Asn | Arg | Val | Glu | Tyr |
| VPA DS1 | pSVeDS1 | Val | Ser | Glu | Ser | Lys | Asn |

TABLE 3

| | Expression Vector | Amino acid number from N-terminus | | | | | | | | | |
|---|---|---|---|---|---|---|---|---|---|---|---|
| | | 35 | 36 | 37 | 38 | 39 | 40 | 41 | 42 | 43 | 44 |
| TPA | pSVeCPA-1 (SEQ ID NO 35) | Trp | Cys | Asn | Ser | Gly | Arg | Ala | Gln | Cys | His |
| VPAs | | | | | | | | | | | |
| SD1 | pSVeSD1 (SEQ ID NO 36) | Trp | Cys | Ser | Val | Val | Glu | Ser | Ser | Cys | His |
| SD2 | pSVeSD2 (SEQ ID NO 37) | Trp | Cys | Leu | Val | Val | Ile | Val | Leu | Cys | His |
| SD3 | pSVeSD3 (SEQ ID NO 38) | Trp | Cys | Ser | Val | Val | Ile | Ser | Ser | Cys | His |
| SD4 | pSVeSD4 (SEQ ID NO 39) | Trp | Cys | Ser | Val | Val | Ile | Val | Ser | Cys | His |
| SD5 | pSVeSD5 (SEQ ID NO 40) | Trp | Cys | Ser | Val | Val | Ile | Val | Leu | Cys | His |
| SD6 | pSVeSD6 (SEQ ID NO 41) | Trp | Cys | Phe | Leu | Phe | Val | Leu | Phe | Cys | His |
| SD7 | pSVeSD7 (SEQ ID NO 42) | Trp | Cys | Val | Phe | Leu | Phe | Ile | Val | Cys | His |
| SD8 | pSVeSD8 (SEQ ID NO 43) | Trp | Cys | Ser | Val | Val | Glu | Phe | Ser | Cys | His |
| SD9 | pSVeSD9 (SEQ ID NO 44) | Trp | Cys | Ser | Val | Val | Glu | Phe | Gln | Cys | His |
| SD10 | pSVeSD10 (SEQ ID NO 45) | Trp | Cys | Ser | Val | Val | Glu | Ser | Gln | Cys | His |

The corresponding expression vectors pSVePN1, pSVePN2, pSVePN3, pSVeDS1, pSVeSD1, pSVeSD2, pSVeSD3, pSVeSD4, pSVeSD5, pSVeSD6, pSVeSD7, pSVeSD8, pSVeSD9 and pSVeSD10, used for the production of these VPAs, were constructed as follows.

Among the aforesaid expression vectors, pSVePN1, pSVePN2 and pSVePN3 were constructed by using T4 DNA ligase to ligate the three types of DNA fragments obtained in the following items 1, 2, and 3.

(1) Synthetic DNA fragments

Single-stranded synthetic DNA fragments for use in the construction of the expression vectors for the respective VPAs, two varieties for each vector, were synthesized with a commercial DNA synthesizer (381A DNA Synthesizer, Applied Biosystems). The DNA sequences of these synthetic oligonucleotides are shown below. The two varieties of single-stranded DNA corresponding to each vector are complementary. Prior to the construction of the expression vector, these DNA fragments were annealed by a conventional method for use in the form of double-stranded DNA.

Synthetic DNA fragments (SEQ ID NOS: 1 and 2) for construction of pSVePN1

5' GATCTTACCAAGTGATCTGCAAGAAGAAGAAAACGCAGATGATATACCAGCAACATCAGTCATG 3'
5' ACTGATGTTGCTGGTATATCATCTGCGTTTTCTTCTTCTTGCAGATCACTTGGTAA 3'

Synthetic DNA fragments (SEQ ID NOS: 3 and 4) for construction of pSVePN2

-continued
```
5' GATCTTACCAAGTGATCTGCAGAGATGAAGAGGTCTCCTCCTCCTACCAGCAACATCAGTCATG 3'
5' ACTGATGTTGCTGGTAGGAGGAGGAGACCTCTTCATCTCTGCAGATCACTTGGTAA 3'
```

Synthetic DNA fragments (SEQ ID NOS: 5 and 6) for construction of pSVePN3

```
5' GATCTTACCAAGTGATCTGCAGAGATGAAAAAACGCAGATGATATTCTCCTCTGAGTCCTCATG 3'
5' AGGACTCAGAGGAGAATATCATCTGCGTTTTTTCATCTCTGCAGATCACTTGGTAA 3'
```

(2) NlaIII-NarI fragment of pSVeCPA-1

The smaller of the DNA fragments (BglII-NarI fragment, approximately 0.33 kb) obtained by digestion with BglII and NarI of the TPA expression vector pSVe-CPA-1, constructed as in item II-A above, was digested with NlaIII, which cleaves the base sequence of the cDNA encoding TPA in the vicinity of the 250th base pair, thus obtaining an NlaIII-NarI fragment of approximately 265 bp.

(3) BglII-NarI fragment of pSVeCPA-1

The larger of the DNA fragments (BglII-NarI fragment, approximately 8.1 kb) was obtained by digestion with BglII and NarI of the TPA expression vector pSVeCPA-1 constructed as in item II-A above.

Three expression vectors (pSVePN1, pSVePN2 and pSVePN3) for producing the corresponding VPAs were constructed by ligation of the DNA fragments 1, 2, and 3 obtained in this manner. Transformants were then obtained by introducing these expression vectors into E. coli DH1 (ATCC 33849).

The expression vector pSVeDS1 (production for DS1) was constructed by using T4 DNA ligase to ligate the following four types of DNA fragments 4, 5, 6, and 7.

(4) Synthetic DNA fragments

Single-stranded synthetic DNA fragments for use in the construction of the expression vectors for the respective VPAs, two varieties for each vector, were synthesized with a commercial DNA synthesizer (381A DNA Synthesizer, Applied Biosystems). The sequences of these synthetic oligonucleotides are shown below. The two varieties of single-stranded DNA corresponding to each vector are complementary, and prior to the construction of the expression vector were annealed by a conventional method for use in the form of double-stranded DNA.

Synthetic DNA fragments (SEQ ID NOS: 7 and 8) for construction of DS1:

```
5' TCTTGGACTCAGAGACTC 3'
5' TCAGAGTCTCTGAGTCCAAGA 3'
```

(5) BglII-DdeI fragment of pSVeCPA-1

The smaller of the DNA fragments (BglII-NarI fragment, approximately 0.33 kb) obtained by digestion with BglII and NarI of the TPA expression vector pSVeC-PA-1, constructed as in item II-A above. This BglII-NalI fragment was digested with DdeI, which cleaves the cDNA sequence encoding TPA in the vicinity of the 270th base pair, thus obtaining a BglII-DdeI fragment of approximately 80 bp.

(6) SspI-NarI fragment of pSVeCPA-1

The BglII-NarI fragment (0.33 kb) obtained as in item II-B (5) above was digested with SspI, which cleaves the base sequence of the cDNA encoding TPA in the vicinity of the 290th base pair, thus obtaining an SspI-NarI fragment of approximately 230 bp.

(7) BglII-NarI fragment of pSVeCPA-1

The larger of the DNA fragments (approximately 8.1 kb) was obtained by digestion with BglII and NarI of the TPA expression vector pSVeCPA-1, constructed as in item II-A above.

The expression vector pSVeDS1 was constructed by ligation of the DNA fragments 4, 5, 6, and 7 obtained in this manner. A transformant was obtained by introduction of this VPA expression vector into an E. coli DH1 (ATCC 33849).

The aforesaid expression vectors pSVeSD1, pSVeSD2, pSVeSD3, pSVeSD4, pSVeSD5, pSVeSD6, pSVeSD7, pSVeSD8, pSVeSD9, and pSVeSD10 were constructed by using T4 DNA ligase to ligate the following four types of DNA fragments 8, 9, 10, and 11.

(8) Synthetic DNA fragments

Single-stranded synthetic DNA fragments for use in the construction of the expression vectors for the respective VPAs, two varieties for each vector, were synthesized with a commercial DNA synthesizer (381A DNA Synthesizer, Applied Biosystems). The sequences of these synthetic oligonucleotides are shown below. The two varieties of single-stranded DNA corresponding to each vector are complementary, and prior to the construction of the expression vector were annealed by a conventional method for use in the form of double-stranded DNA.

Synthetic DNA fragments (SEQ ID NOS: 9 and 10) for construction of pSVeSD1

```
5' GTGGCAGGAGGACTCCACCACAGAGCACCAGCAAT 3'
5' ATTGCTGGTGCTCTGTGGTGGAGTCCTCCTGCCACTCA 3'
```

Synthetic DNA fragments (SEQ ID NO: 11 and 12) for construction of pSVeSD2

```
5' GTGGCACAGCACAATCACCACCAGGCACCAGCAGT 3'
5' ACTGCTGGTGCCTGGTGGTGATTGTGCTGTGCCACTCA 3'
```

Synthetic DNA fragments (SEQ ID NO: 13 and 14) for construction of pSVeSD3

```
5' GTGGCAGGAGGAGATCACCACAGAGCACCAGCAGT 3'
5' ACTGCTGGTGCTCTGTGGTGATCTCCTCCTGCCACTCA 3'
```

Synthetic DNA fragments (SEQ ID NO: 15 and 16) for construction of pSVeSD4

```
5' GTGGCAGGAGACAATCACCACAGAGCACCAGCAGT 3'
5' ACTGCTGGTGCTCTGTGGTGATTGTCTCCTGCCACTCA 3'
```

-continued

Synthetic DNA fragments (SEQ ID NOS: 17 and 18) for construction of pSVeSD5

5' GTGGCACAGCACAATCACCACAGAGCACCAGCAGT 3'
5' ACTGCTGGTGCTCTGTGGTGATTGTGCTGTGCCACTCA 3'

Synthetic DNA fragments (SEQ ID NOS: 19 and 20) for construction of pSVeSD6

5' GTGGCAGAACAGCACAAACAGGAAGCACCAGCAGT 3'
5' ACTGCTGGTGCTTCCTGTTTGTGCTGTTCTGCCACTCA 3'

Synthetic DNA fragments (SEQ ID NOS: 21 and 22) for construction of pSVeSD7

5' GTGGCAGACAATGAACAGGAAGACACACCAGCAGT 3'
5' ACTGCTGGTGTGTCTTCCTGTTCATTGTCTGCCACTCA 3'

Synthetic DNA fragments (SEQ ID NOS: 23 and 24) for construction of pSVeSD8

5' GTGGCAGGAAAACTCCACCACAGAGCACCAGCAAT 3'
5' ATTGCTGGTGCTCTGTGGTGGAGTTTTCCTGCCACTCA 3'

Synthetic DNA fragments (SEQ ID NOS: 25 and 26) for construction of pSVeSD9

5' GTGGCACTGAAACTCCACCACAGAGCACCAGCAGT 3'
5' ACTGCTGGTGCTCTGTGGTGGAGTTTCAGTGCCACTCA 3'

Synthetic DNA fragments (SEQ ID NOS: 27 and 28) for construction of pSVeSD10

5' GTGGCATTGGGATTCCACCACAGAGCACCAGCAGT 3'
5' ACTGCTGGTGCTCTGTGGTGGAATCCCAATGCCACTCA 3'

(9) BglII-SspI fragment of pSVeCPA-1

The TPA expression vector constructed as in item II-A above was digested with BglII and NarI, and the smaller DNA fragment (BglII-NarI fragment, approximately 0.33 kb) was recovered. This BglII-NarI fragment was digested with SspI, which cleaves the base sequence of the cDNA encoding TPA in the vicinity of the 290th base pair, thereby obtaining a BglII-SspI fragment of approximately 100 bp.

(10) DraIII-NarI fragment of pSVeCPA-1

The BglII-NarI fragment of approximately 0.33 kb obtained as in item II-B, 9 above was digested with DraIII, which cleaves the base sequence of the cDNA encoding TPA in the vicinity of the 320th base pair, thus obtaining a DraIII-NarI fragment of approximately 200 bp.

(11) BglII-NarI fragment of pSVeCPA-1

The larger DNA fragment (BglII-NarI fragment, approximately 8.1 kb) was obtained by digestion with BglII and NarI of the TPA expression vector pSVeCPA-1 constructed as in item II-A above.

Eight expression vectors (pSVeSD1, pSVeSD2, pSVeSD3, pSVeSD4, pSVeSD5, pSVeSD6, pSVeSD7, pSVeSD8, pSVeSD9, and pSVeSD10) were constructed by ligation of the four types of DNA fragments 8, 9, 10, and 11 obtained in this manner. Transformants were obtained by introducing these expression vectors into E. coli DHI (ATCC JJ846). A transformant carrying the expression vector pSVeSD4 was designated E. coli DH1SD 459, and deposited with the Fermentation Research Institute, Agency of Industrial Science and Technology, 1-3, Higashi 1-chome, Tsukabashi, Ibaraki-ken, Japan, on Jan. 31, 1990, under Accession No. BP-3082, where it will be maintained under the terms of the Budapest Treaty.

(II-C) Construction of expression vectors for VPAs with modified kringle 1 region Expression vectors pSCKM4 and pSCKM21 for the TPA kringle 1 regions, were constructed as follows. Amino acid replacements of KM4 and KM21 are shown in Table 4.

TABLE 4

| | Expression Vector | Amino Acid number from N-terminus | | | |
|---|---|---|---|---|---|
| | | 115 | 161 | 162 | 165 |
| TPA VPAs | pSVeCPA-1 | Asn | Gly | Lys | Ser |
| KM4 | pSCKM4 | — | Arg | Arg | Trp |
| KM21 | pSCKM21 | Pro | — | — | — |

(1) Preparation of vector M13NS for introduction of mutations

The TPA expression vector pSVeCPA-1 was cleaved with restriction enzymes NarI (New England Biolabs) and SmaI (Takara Shuzo, Co., Ltd.), and a fragment of approximately 1.2 kb was isolated by agarose gel electrophoresis. This fragment contains a cDNA sequence encoding an amino acid sequence of TPA from the glycine residue at the 110th position to the proline residue at the 508th position. Using T4 DNA ligase, this approximately 1.2 kb fragment was ligated to M13mp11 (Takara Shuzo, Co., Ltd.) which had been cleaved with NarI and SmaI, thereby obtaining a vector M13-NS. This vector was introduced into E. coli JM109 (Takara Shuzo, Co., Ltd.), resulting in a transformant.

(2) Site-directed amino acid replacements

The transformants possessing the vector M13-NS obtained as in item II-C, 1 were cultivated, and single-stranded DNA was obtained from the supernate of the culture medium. Next, in order to construct the expression vector pSCKM4 for KM4, the following DNA fragment I (SEQ ID No. 29) was synthesized with a commercial DNA synthesizer (381A DNA Synthesizer, Applied Biosystems).

5'
  TGCTGCAGAACTCCCAGCT-
  GTACCTCCTCGCCTTAAAGACG 3'    (I)

This DNA fragment was phosphorylated with T4 polynucleotide kinase (Takara Shuzo, Co., Ltd.), then annealed to the aforesaid single-stranded DNA M13-

NS, and the DNA chain was extended. This procedure was accomplished by means of a commercial in vitro mutageneric system kit (Amersham). The plasmid (M13-NSM4) containing the desired mutant portion, obtained in this manner was introduced into E. coli TG1 and amplified. Thus, the DNA sequence of the original expression vector corresponding to the amino acid sequence from the 161st through the 165th residue of TPA (glycine, lysine, tyrosine, serine, serine), i.e., -GGGAAGTACAGCTCA-, was converted into -AGGAGGTACAGCTGG-. This DNA sequence corresponds to the amino acid sequence arginine, arginine, tyrosine, serine, tryptophan. The introduction of the aforesaid mutation in the DNA sequence was confirmed by means of a commercial sequencing kit (Takara Shuzo, Co., Ltd.).

Next, in order to construct an expression vector pSCKM21 for the VPA KM21, the following DNA fragment (II) (SEQ ID No. 30) was synthesized with a commercial DNA synthesizer (381A DNA Synthesizer, Applied Biosystems).

5' GCTGTTCCAGGGGGTGCACTCG 3'    (II)

Using this DNA fragment II, the mutant vector M13-NSM21 was prepared by the same procedure as that described above.

(3) Preparation of expression vectors for VPAs with modified kringle regions

After preparation of the double-stranded form of the plasmid M13-NSM4 obtained as in the aforesaid item II-C, 2, this DNA was cleaved with NarI and SmaI, and a fragment of approximately 1.2 kb (smaller fragment) was obtained by agarose gel electrophoresis. Next, the TPA expression vector pSVeCPA-1 was also treated with NarI and SmaI, and a fragment of approximately 7 kb (larger fragment) was obtained by agarose gel electrophoresis. An expression vector pSCKM4 for KM4 was then obtained by ligation of these two fragments. Similarly, using M13-NSM21 in place of M13-NSM4, an expression vector pSCKM21 was obtained and introduced into E. coli DH1. This vector comprises a gene encoding the VPA KM21. Transformants were obtained by introduction of pSCKM4 and PSCKM21 into E. coli DH1 (ATCC 33849), respectively.

(II-D) Construction of expression vectors for VPA with modifications in both finger and kringle regions Expression vectors pSVeKS48 and pSVeKS218 for the VPAs KS48, and KS218, respectively, with amino acid replacements in both the finger region and the kringle 1 region, were constructed as follows. Amino acid replacements in these VPAs are shown in Table 5.

PSVeSD8 was treated with BglII and NarI, and the smaller fragment (approximately 0.33 kb) was isolated. Similarly, pSCKM4 was treated with BglII and NarI, and the larger fragment (approximately 8.1 kb) was isolated. These two fragments were ligated with T4 DNA ligase, thereby obtaining an expression vector pSVeKS48, and transformants were obtained by introducing this vector into E. coli DH1 (ATCC No. 33849). A transformant carrying the expression vector pSVeKS48 was designated E. coli DH1 KS48, and deposited with the Fermentation Research Institute, Agency of Industrial Science and Technology, 1-3, Higashi 1-chome, Tsukubashi, Ibaraki-ken, Japan, on Jun. 25, 1990, under Accession No. BP-3083, where it will be maintained under the terms of the Budapest Treaty.

Separately, the smaller fragment (approximately 0.33 kb) obtained by treatment of pSVeSD8 with BglII and NarI was isolated, while pSCKM21 was also treated with BglII and NarI and the larger of the resulting fragments (approximately 8.1 kb) was isolated. An expression vector pSVeKS218 was obtained by ligation of these two fragments with T4 DNA ligase. Transformants were obtained by introducing this vector into E. coli DH1 (ATCC No. 33849).

(III) Construction of marker vector pSV2neo-dhfr

Marker vectors possessing the neo and dhfr genes as selectable markers were constructed in the following manner.

First, the rDNA vector pSV2dhfr (ATCC, rDNA Vector 37146) was cleaved with a restriction enzyme PvuII, and a PvuII-PvuII fragment was isolated. Using T4 DNA ligase, this PvuII-PvuII fragment was ligated with BamHI linker-d (pCGGATCCG, Takara Shuzo, Co., Ltd.), thereby constructing a vector pSV2Bdhfr, which was introduced into E. coli DH1 and amplified. This vector pSV2Bdhfr was isolated and digested with BamHI, and a BamHI-BamHI fragment (approximately 2 kb) containing dhfr gene was then isolated by agarose gel electrophoresis. Using T4 DNA ligase, this BamHI-BamHI fragment was ligated to a BamHI-BamHI fragment obtained by cleavage of the rRNA vector pSV2neo (American Type Culture Collection, rDNA Vector 37149). The circular marker vector constructed in this manner was introduced into E. coli DH1. In this marker vector, which was designated pSV2neo-dhfr, the neo and dhfr genes are inserted in the same expression direction.

(IV) Transformation of cultured animal cells and production of VPAs

Cultured animal cells of the line CHO-K1 (ATCC CCL-61) were selected as the host cells, and transformed using the various VPA expression vectors obtained as in the aforesaid item II-B, in accordance with the method of Chen, C. et al. [Molecular and Cellular Biology, 7, 2745 (1987)]. Each of these VPA expression vectors was used in a mixture with the marker vector pSV2neo-dhfr in a ratio of 300:1 [VPA expression vector:pSV2neo-dhfr(by weight)]. A coprecipitate of the vector mixture and calcium phosphate was then added to CHO-K1 cells (5×10⁵ cells/10 ml medium/10 cm diameter petri dish) previously grown in MD medium (MCDB302:modified Dulbecco's MEM=1:1, Sigma) with 5% of added fetal calf serum (FCS), and after 15 hours of cultivation, the medium was replaced with

TABLE 5

| | Expression Vector | Amino acid number from N-terminus | | | | | | | | | |
|---|---|---|---|---|---|---|---|---|---|---|---|
| | | 37 | 38 | 39 | 40 | 41 | 42 | 115 | 161 | 162 | 165 |
| TPA | pSVeCPA1 | Asn | Ser | Gly | Arg | Ala | Gln | Asn | Gly | Lys | Ser |
| VPAs | | | | | | | | | | | |
| KS48 | pSVeKS48 | Ser | Val | Val | Glu | Phe | Ser | Asn | Arg | Arg | Trp |
| KS218 | pSVeKS218 | Ser | Val | Val | Glu | Phe | Ser | Pro | Gly | Lys | Ser | fresh medium of the same type. After a further 48 hours of cultivation, the medium was replaced by MD medium containing 5% FCS, 400 μg/ml G418 sulfate (Gibco), 7 mM ε-aminocaproic acid, and 50 μM foipan (Ono Pharmaceutical Co.). Then, cultivation was continued for a further 2 weeks, after which the G418-resistant strains were isolated. These G418-resistant strains were transferred to 12-well multidishes (Linbrow Co.), and cultivated over the entire base area of the dishes for 24 hours in the aforesaid MD medium. The content of VPA in this culture broth was quantitated by activity measurements, using fibrin plates containing plasminogen [Mackie, M., et al., British Journal of Hematology, 47, 77 (1981)]. Protein-assayed preparations of VPAs, purified as described in item V below, were used for this quantitation. With respect to each transformant, cultures producing TPA in a concentrations of at least 0.5 μg/ml per milliliter culture medium were selected. The transformant cells thus selected produced VPAs even in serum-free MD medium (MD medium containing 7 mM ε-aminocaproic acid, 50 μM foipan, 1 mg/ml bovine serum albumin, and 5 μg/ml insulin).

(V) SDS-PAGE followed by fibrin zymography

To determine the apparent molecular weight of each VPA, serum free culture medium was subjected to SDS-PAGE followed by fibrin zymography in accordance with the method of Granelli-Piperno A. et al. [Journal of Experimental Medicine, 148, 223–34 (1978)]

Figure 7A:
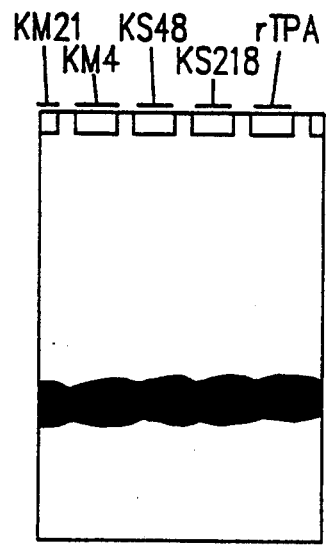
FIGS. 7A, 7B and 7C shows the results of SDS-PAGE followed by fibrin zymography of VPAs.
Figure 7B:
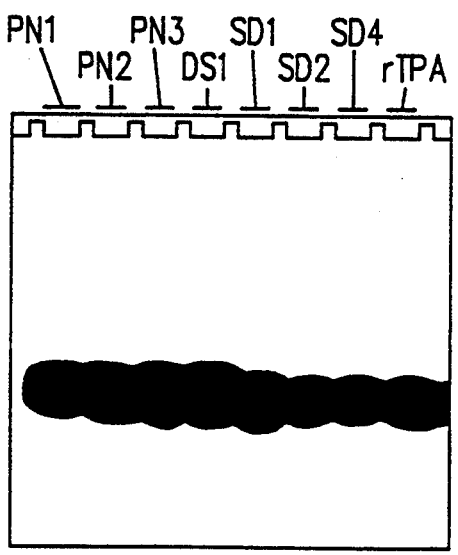
Figure 7C:
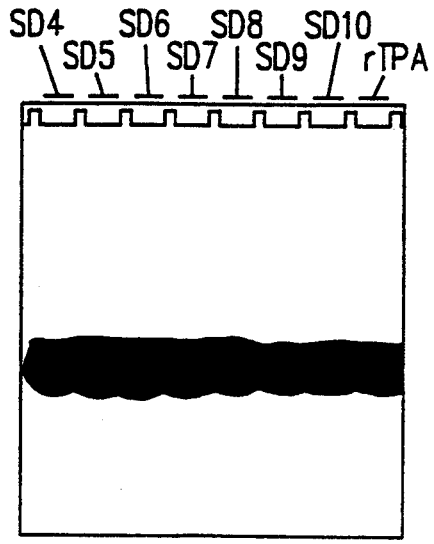
Figure 8A:
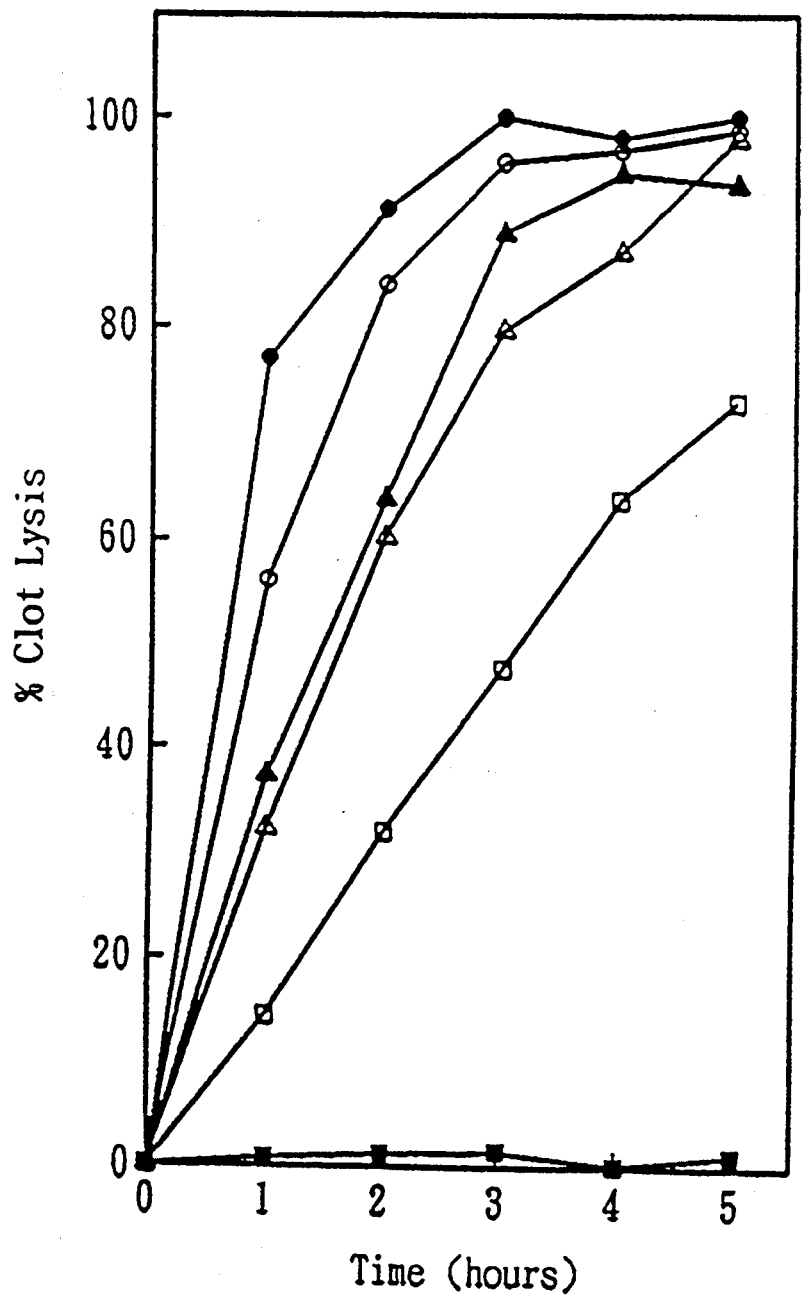
FIG. 8A–D shows the results of the evaluation of in vitro thrombolytic ability of VPAs; SD4, KS218, and KS48 of the present invention.
Figure 8B:
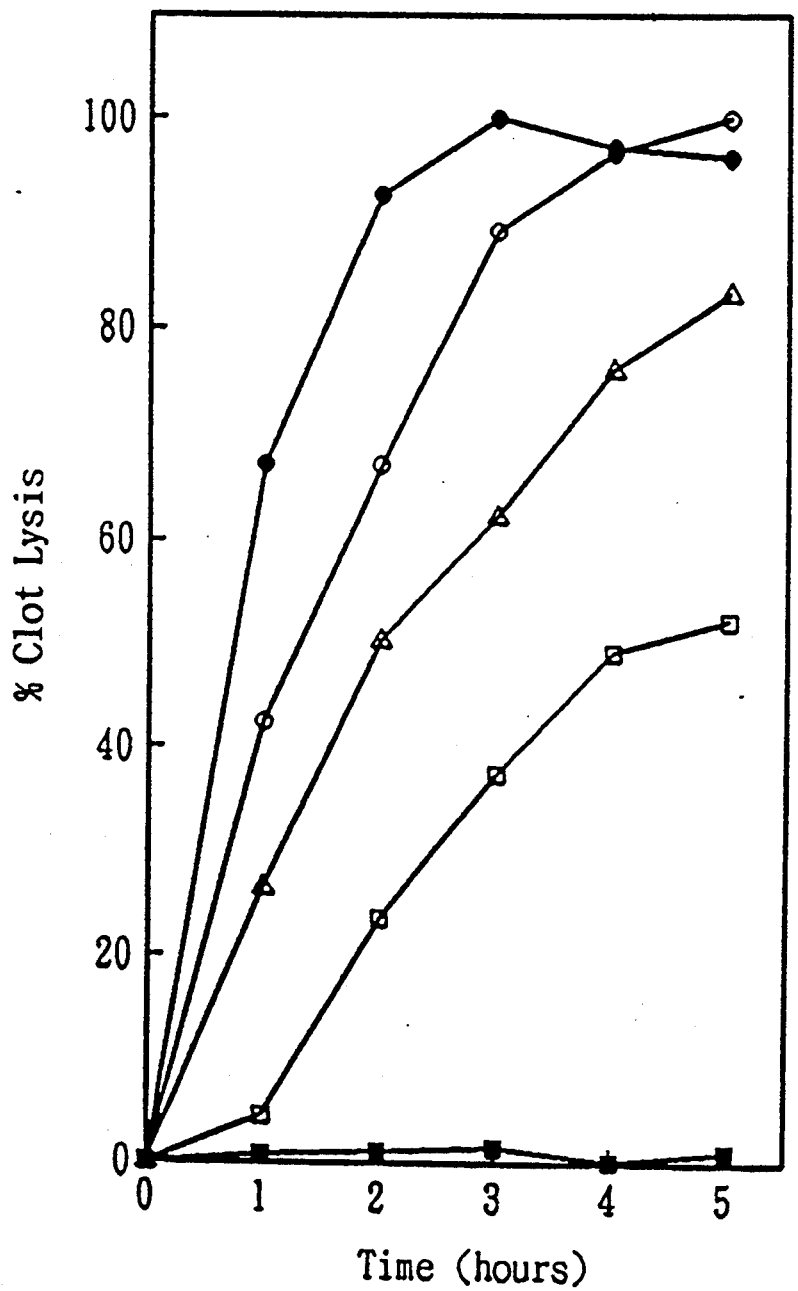
Figure 8C:
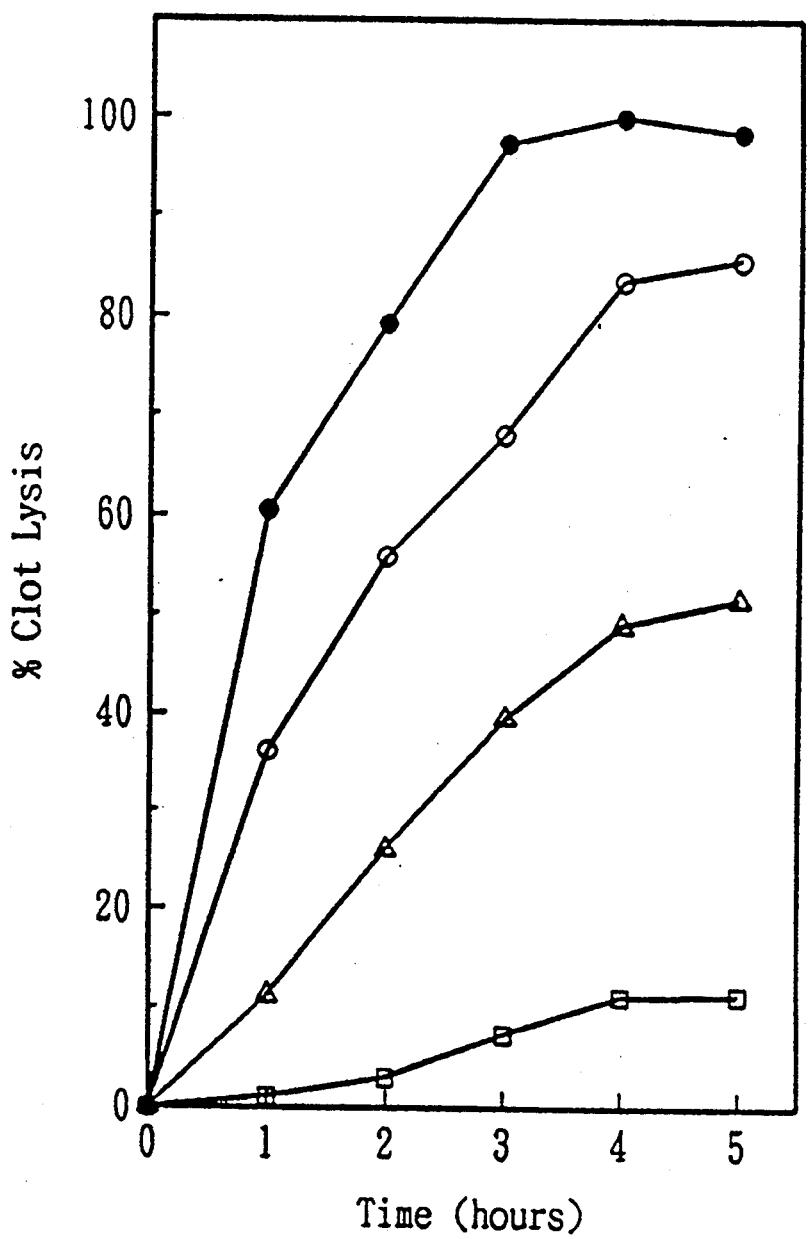
Figure 8D:
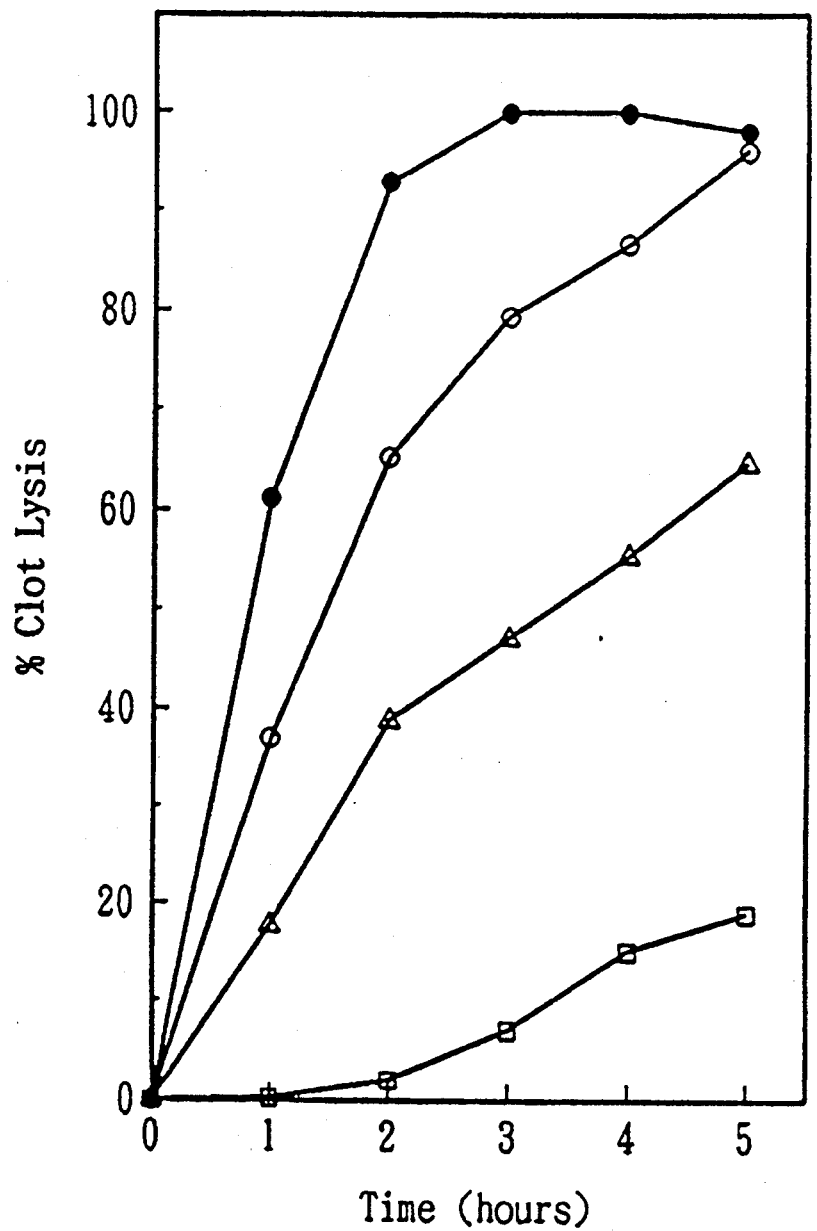

Samples of conditioned medium were boiled in 0.1% SDS and seperated on 7.5% slab gels under non-reducing conditions. The gels were washed two times in 2% Triton X100 and overlayed on a fibrin-agarose plate. The plate was incubated at 37° C. untill visual zones of lysis appeared. The results so obtained were shown in FIG. 7. Lyric bands with the same mobility as rTPA were observed for all VPAs.

(VI) Protein Purification

Expression vector pSVePA-1 containing TPA gene were transfected into CHO K1 cells as described in item above, and cell lines secreting rTPA (reffered to as rTPA) was established (Japanese Laid-Open Patent Publication No. 62-14783). Conditioned media containing VPAs or rTPA were harvested and purified by five column chromatographic steps. The harvest medium was loaded onto a controlled pore glass (CPG-10, CPG Inc.) column equilibrated with 20 mM sodium phosphate buffer, containing 1M NaCl and 10 KIU/ml aprotinin (pH7.5). After washing with 2 volumes of the same buffer, the bound protein was eluted with 20 mM sodium phosphate buffer containing 1M NaCl, 0.5M KSCN, 1M ε-aminocaproic acid and 10 KIU/ml aprotinin (pH7.5). The eluate was loaded onto Con A-Sepharose (Pharmacia LKB Biotechnology) equilibrated with 20 mM sodium phosphate buffer containing 1M NaCl and 0.01% Tween 80 (pH7.5). After washing with 10 volumes of equilibration buffer, the bound protein was eluted with a linear gradient from 0–0.4M α-methylmannoside in the equilibration buffer. The eluate was dialyzed and loaded onto a DEAE-Sepharose (Pharmacia LKB Biotechnology) column equilibrated with 20 mM Tris-HCl, 0.1M ε-aminocaproic acid, and 0.01% Tween 80 (pH7.5). After washing with the same buffer, the column was eluted with a linear gradient from 0–0.4M NaCl in equilibration buffer. The eluate was dialyzed and loaded onto a Phenyl-Sepha-rose CL4B (Pharmacia LKB Biotechnology) column equilibrated with 20 mM sodium phosphste buffer containing 1.0M NaCl and 0.1M arginine (pH7.5). After washing with the equilibration buffer, a linear gradient from 0 to 50% ethylene glycol in equilibration buffer was applied. The eluate was then dialyzed and concentrated using an Amicon filter and loaded onto Sephacryl S-200 (Pharmacia LKB Biotechnology) equilibrated with arginine-phosphate buffer containing 0.1M phosphate, 0.2M arginine and 0.008% Tween 80 (pH7.3). The protein concentration was determined by the method of Lowry et al. The results demonstrated that approximately 1–3 mg of each VPA was obtained from 2–6 liters of culture media after cultivating of the corresponding transformant.

Example 2

Measurement of plasminogen activation ability

The plasminogen activation ability of KM4 and KS48 was compared with that of rTPA. The measurements were performed by the following procedure, in accordance with the method of Takada et al., employing the synthetic substrate S-2251 on which plasmin acts [Takada, A., et al., Haemostasis, 18, 117 (1988)]. The TPA was used in the reaction after conversion to two-chain form, and the plasminogen used was human lysine type plasminogen (American Diagnostica).

Lysine type plasminogen was added at concentrations in the range of 11–88 nM to aliquots of 20 mM phosphate buffer solution (pH 7.5) containing 0.1M sodium chloride, 0.05% Tween 80, 0.3 mM S-2251, and 0.1 mg/ml cyanogen bromide-treated human fibrinogen. The aforesaid VPAs (KM4 or KS48) were added to aliquots of this solution in amounts so that the concentrations of the respective VPAs would be 0.15 nM, and thus, the reaction was initiated. The reaction was conducted at 25° C., and the absorbance at 405 nm was measured at predetermined times. The rate of plasmin generation was determined from the obtained data. A Lineweaver-Burk graph was plotted using this plasmin generation rate, and the parameters Km and Kcat were calculated. The results so obtained are shown in Table 6. The data in this Table show that each of the tested VPAs of the present invention displayed higher plasminogen activation ability than rTPA.

TABLE 6

| | Km(nM) | $V_{MaN}$(nM · min) | Kcat(sec$^{-1}$) | Kcat/Km(nM · sec$^{-1}$) |
|---|---|---|---|---|
| rTPA | 41.5 | 0.784 | 0.0871 | 0.00210 |
| VPAs | | | | |
| KM4 | 29.2 | 1.92 | 0.213 | 0.00729 |
| KS48 | 32.8 | 0.72 | 0.0800 | 0.00244 |

Example 3

Measurement of in vitro thrombolytic ability

Ability of the VPAs obtained in Example 1 (KS218, SD4 and KS48) for the lysis of plasma clot was measured in accordance with the method of Collen, D. et al. [Thromb. Haemost., 52, 308 (1984)], using the following procedure.

First, plasma was prepared from the blood of five volunteers using a citrate anticoagulant, then these plasmas were mixed and used for the following measurements. To 1 ml aliquots of plasma were added 10 μl of $^{125}$I-labelled fibrinogen (10 MBq/ml), 25 μl of human α-thrombin (100 units/ml) and 50 μl of 0.5M calcium chloride, then the mixture was promptly placed in a silicone tube (inner diameter 4 mm, outer diameter 8 mm) and allowed to coagulate for 1 hour at 37° C. The silicone tube containing the clot so formed was cut into 1 cm lengths, after which the clots were removed from the tube and washed with 0.85% sodium chloride solution.

Each of the plasma clots prepared in this manner was floated in 2.5 ml of plasma, then the VPAs to be tested was added, allowing the reaction to be initiated. After the commencement of the reaction, 50 μl of the plasma was sampled every hour, and the radioactivity of the $^{125}$I which had been released from the plasma clot into the plasma was measured with a gamma-counter. This measurement was continued over a 5-hour period. Taking the radioactivity released by complete dissolution of the clot as 100%, the percentage of dissolution for each sampling time was determined. The results so obtained are shown in FIG. 8. rTPA was used as a control. 50% lysis at 2 hr were 70 ng/ml for rTPA, 100 ng/ml for SD4, 140 ng/ml for KS218, and 185 ng/ml for KS48. In this figure, the results for the respective analytes are indicated by the symbols: A; rTPA, B; SD4, C; KS48, D; KS218, □; 40 ng/ml, Δ; 100 ng/ml,  ; 140 ng/ml,  ; 200 ng/ml,  ; 500 ng/ml, . ; Spontaneous lysis.

Example 4

Pharmacokinetics Of VPAs in rabbits

Figure 9:
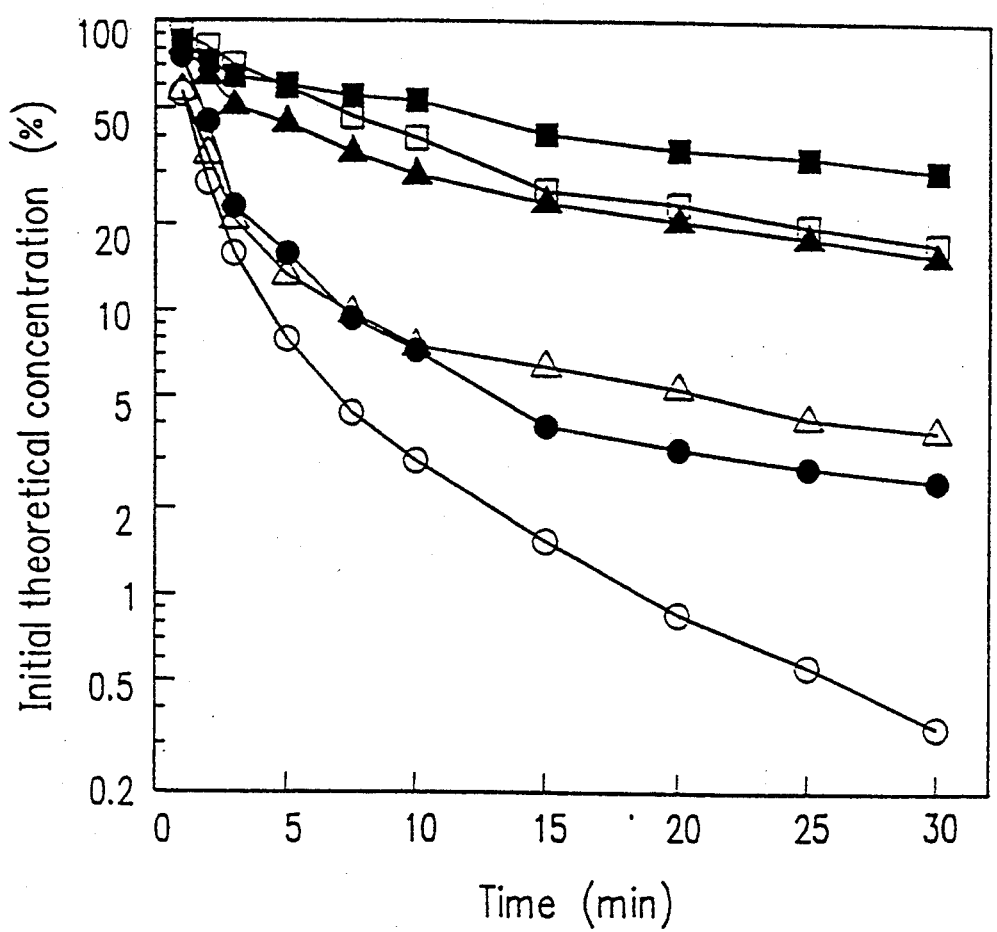
FIG. 9 shows the in vivo clearance of VPAs; PN1, PN2, PN3, DS1, and SD4 of the present invention in rabbit blood.
Figure 10:
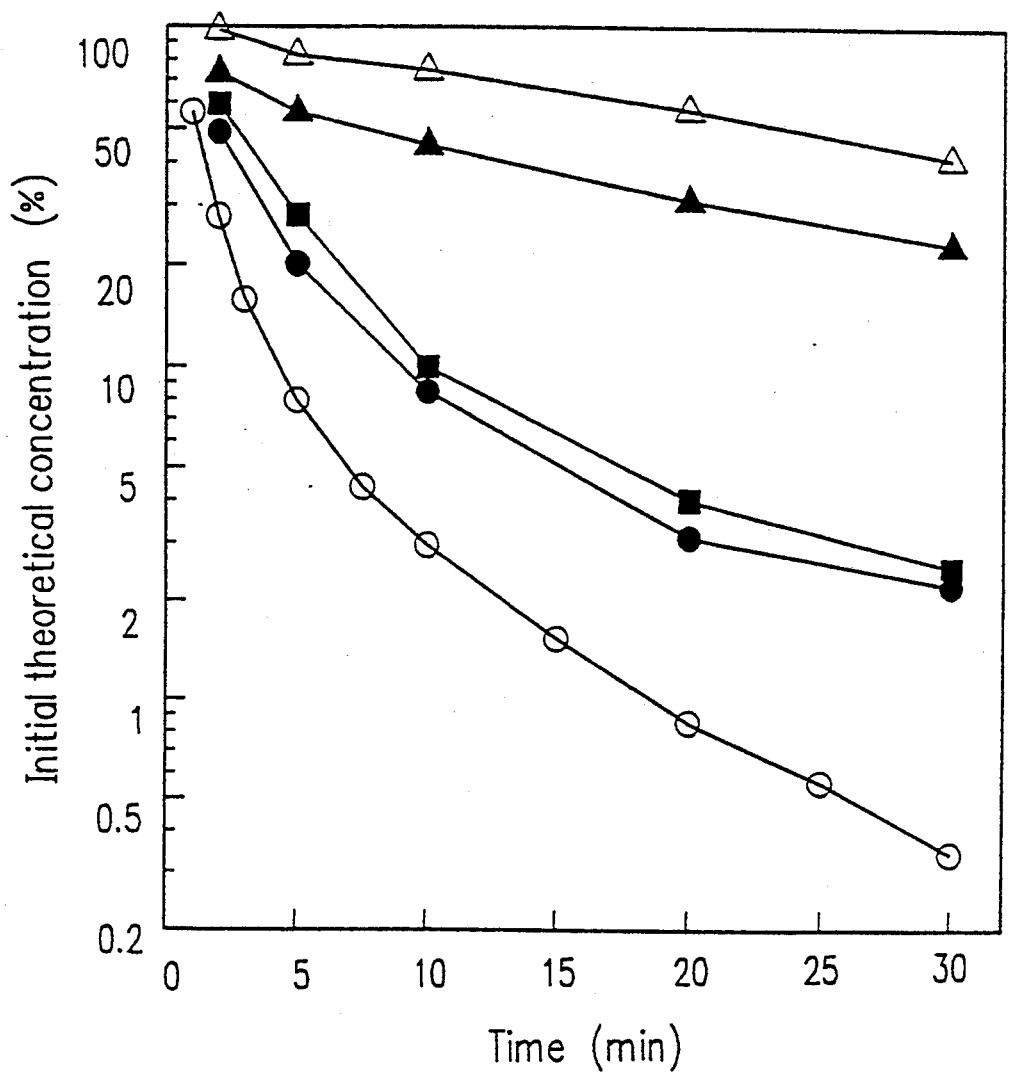
FIG. 10 shows the in vivo clearance of VPAs; KM4, KM21, KS48, and KS218 of the present invention in rabbit blood.
Figure 11:
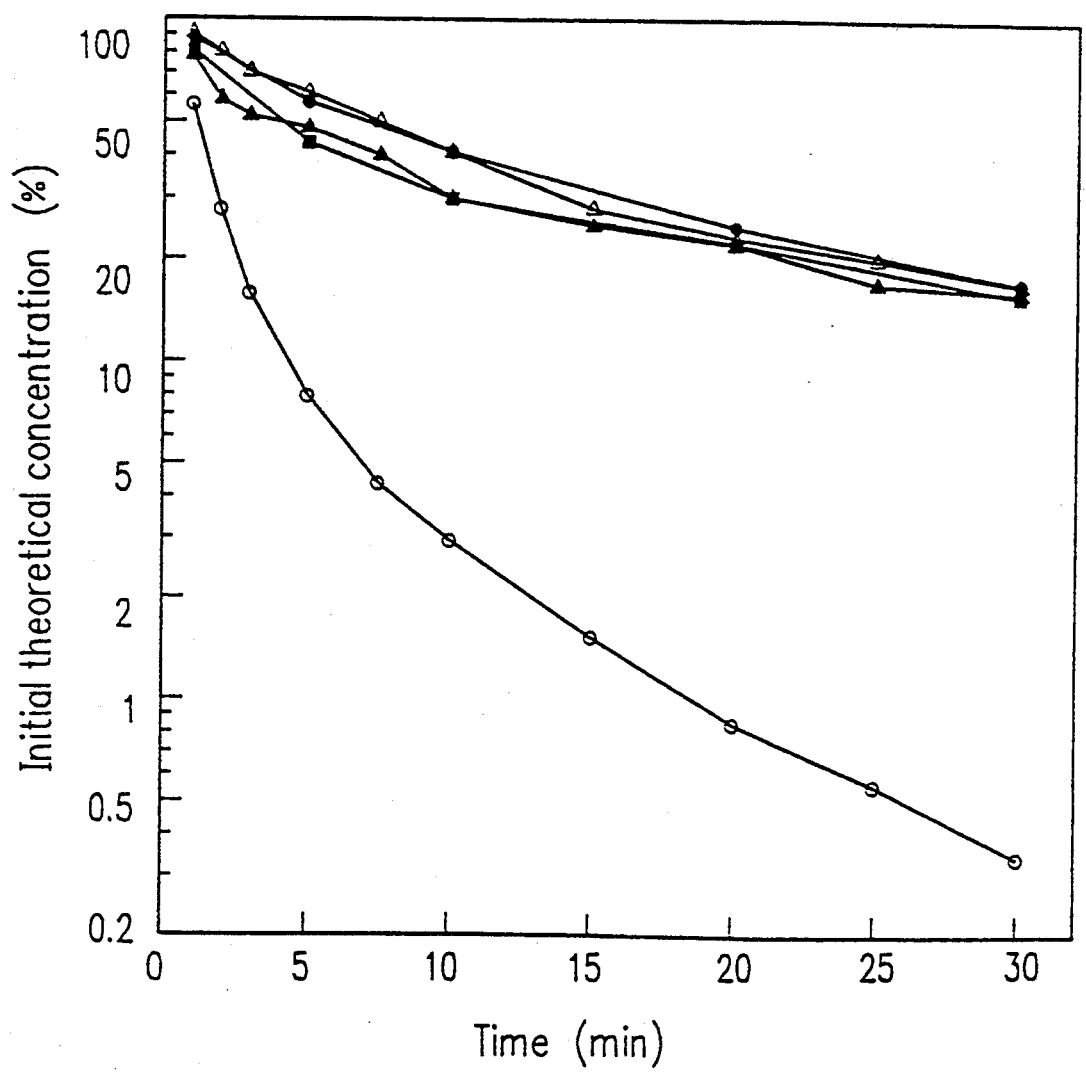
FIG. 11 shows the in vivo clearance of VPAs; SD1, SD8, SD9, and SD10 of the present invention in rabbit blood.

Anesthetized New Zealand white rabbits (body weight about 3 Kg) were infused through the marginal ear vein with a bolus of about 200 mg of TPA of the VPAs. One ml of blood samples were withdrawn from the femoral vein directly into 3.8% sodium citrate. The sampling times for the SD1, SD2, SD3, SD4, SD5, SD6, SD7, SD8, and rTPA were zero, 1, 2, 3, 5, 7.5, 10, 15, 20, 25, 30 min after injection. The sampling times for the KM21, KM4, KS218, and KS48 were zero, 2, 5, 10, 20, and 30 min after injection. The sampling times for the SD9 and SD10 were Zero, 1, 5, 10, 20, and 30 min after injection. Each experiment was examined at n=2. The samples were centrifuged to obtain cell free plasma and frozen until analyzed by ELISA. Kinetics were analyzed using a statistical analysis program as described elsewhere [Yamaoka K. et al. J. Pharmacokin. Biopharm. 6, 547–58 (1978)]. From this results, the times required for plasma concentration to decrease to 50% or 20% were calculated and summerized in Table 7. All VPAs cleared slowly than rTPA. The measurement results for the VPAs PN1, PN2, PN3, DS1, SD4, and rTPA are shown in FIG. 9. In this figure, the results for the respective analytes are indicated by the the symbols:  ; rTPA, □; PN1; Δ; PN2,  ; PN3,  ; DS1,  ; SD4. The measurement results for the VPAs; KM21, KM4, KS48, KS218, and rTPA are shown in FIG. 10. In this figure, the results for the respective analytes are indicated by the symbols:  ; rTPA,  ; KM21,  ; KM4,  ; KS48, Δ; KS218. The measurement results for the VPAs SD1, SD8, SD9, SD10, and rTPA are shown in FIG. 11. In this figure, the results for the respective analytes are indicated by the symbols:  ; rTPA,  ; SD1, Δ; SD8,  ; SD9,  ; SD10.

TABLE 7

|      | 50% (min) | 20% (min) |
|------|-----------|-----------|
| rTPA | 1.7       | 2.6       |
| PN1  | 2.0       | 24        |
| PN2  | 2.5       | 3.9       |
| PN3  | 6.9       | 3.4       |
| DS1  | 20        | >30       |
| SD1  | 4.5       | 23        |
| SD2  | 10        | >30       |
| SD3  | 8.3       | 24        |
| SD4  | 11        | 26        |
| SD5  | 9.6       | 30        |
| SD6  | 14        | >30       |
| SD7  | 12        | 24        |
| SD8  | 7.5       | 26        |
| SD9  | 7.5       | 26        |
| SD10 | 4.5       | 24        |
| KM4  | 4.1       | 6.7       |
| KM21 | 2.8       | 5.0       |
| KS48 | 15        | >30       |
| KS218| 25        | >30       |

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

---

SEQUENCE LISTING ( 1 ) GENERAL INFORMATION:

( i i i ) NUMBER OF SEQUENCES: 45

( 2 ) INFORMATION FOR SEQ ID NO: 1:

( i ) SEQUENCE CHARACTERISTICS:
  ( A ) LENGTH: 64 base pairs
  ( B ) TYPE: nucleic acid
  ( C ) STRANDEDNESS: single
  ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 1:

GATCTTACCA AGTGATCTGC AAGAAGAAGA AAACGCAGAT GATATACCAG CAACATCAGT CATG    64

( 2 ) INFORMATION FOR SEQ ID NO: 2:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 2:

ACTGATGTTG CTGGTATATC ATCTGCGTTT TCTTCTTCTT GCAGATCACT TGGTA    55

( 2 ) INFORMATION FOR SEQ ID NO: 3:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 3:

GATCTTACCA AGTGATCTGC AGAGATGAAG AGGTCTCCTC CTCCTACCAG CAACATCAGT CATG    64

( 2 ) INFORMATION FOR SEQ ID NO: 4:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 4:

ACTGATGTTG CTGGTAGGAG GAGGAGACCT CTTCATCTCT GCAGATCACT TGGTAA    56

( 2 ) INFORMATION FOR SEQ ID NO: 5:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 5:

GATCTTACCA AGTGATCTGC AGAGATGAAA
                              AAACGCAGAT GATATTCTCC TCTGAGTCCT CATG        6 4

( 2 ) INFORMATION FOR SEQ ID NO: 6:

( i ) SEQUENCE CHARACTERISTICS:
          ( A ) LENGTH: 56 base pairs
          ( B ) TYPE: nucleic acid
          ( C ) STRANDEDNESS: single
          ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 6:

AGGACTCAGA GGAGAATATC ATCTGCGTTT TTTCATCTCT GCAGATCACT TGGTAA        5 6

( 2 ) INFORMATION FOR SEQ ID NO: 7:

( i ) SEQUENCE CHARACTERISTICS:
          ( A ) LENGTH: 18 base pairs
          ( B ) TYPE: nucleic acid
          ( C ) STRANDEDNESS: single
          ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 7:

TCTTGGACTC AGAGACTC        1 8

( 2 ) INFORMATION FOR SEQ ID NO: 8:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 8:

TCAGAGTCTC TGAGTCCAAG A        2 1

( 2 ) INFORMATION FOR SEQ ID NO: 9:

( i ) SEQUENCE CHARACTERISTICS:
          ( A ) LENGTH: 35 base pairs
          ( B ) TYPE: nucleic acid
          ( C ) STRANDEDNESS: single
          ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 9:

GTGGCAGGAG GACTCCACCA CAGAGCACCA GCAAT        3 5

( 2 ) INFORMATION FOR SEQ ID NO: 10:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 10:

```
ATTGCTGGTG CTCTGTGGTG GAGTCCTCCT GCCACTCA          38
```

( 2 ) INFORMATION FOR SEQ ID NO: 11:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 11:

```
GTGGCACAGC ACAATCACCA CCAGGCACCA GCAGT          35
```

( 2 ) INFORMATION FOR SEQ ID NO: 12:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 12:

```
ACTGCTGGTG CCTGGTGGTG ATTGTGCTGT GCCACTCA          38
```

( 2 ) INFORMATION FOR SEQ ID NO: 13:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 13:

```
GTGGCAGGAG GAGATCACCA CAGAGCACCA GCAGT          35
```

( 2 ) INFORMATION FOR SEQ ID NO: 14:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 14:

ACTGCTGGTG CTCTGTGGTG ATCTCCTCCT GCCACTCA    38

( 2 ) INFORMATION FOR SEQ ID NO: 15:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 15:

GTGGCAGGAG ACAATCACCA CAGAGCACCA GCAGT    35

( 2 ) INFORMATION FOR SEQ ID NO: 16:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 16:

ACTGCTGGTG CTCTGTGGTG ATTGTCTCCT GCCACTCA    38

( 2 ) INFORMATION FOR SEQ ID NO: 17:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 17:

GTGGCACAGC ACAATCACCA CAGAGCACCA GCAGT    35

( 2 ) INFORMATION FOR SEQ ID NO: 18:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 18:

ACTGCTGGTG CTCTGTGGTG ATTGTGCTGT GCCACTCA   38

( 2 ) INFORMATION FOR SEQ ID NO: 19:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 19:

GTGGCAGAAC AGCACAAACA GGAAGCACCA GCAGT   35

( 2 ) INFORMATION FOR SEQ ID NO: 20:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i i ) MOLECULE TYPE: genomic DNA ( i i i ) HYPOTHETICAL: irrelevant.

( i v ) ANTI-SENSE: no ( i x ) SEQUENCE DESCRIPTION:SEQ ID NO: 20:

ACTGCTGGTG CTTCCTGTTT GTGCTGTTCT GCCACTCA   38

( 2 ) INFORMATION FOR SEQ ID NO: 21:

( i ) SEQUENCE CHARACTERISTICS:
  ( A ) LENGTH: 35 base pairs
  ( B ) TYPE: nucleic acid
  ( C ) STRANDEDNESS: single
  ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 21:

GTGGCAGACA ATGAACAGGA AGACACACCA GCAGT   35

( 2 ) INFORMATION FOR SEQ ID NO: 22:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 22:

ACTGCTGGTG TGTCTTCCTG TTCATTGTCT GCCACTCA   38

( 2 ) INFORMATION FOR SEQ ID NO: 23:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 23:

GTGGCAGGAA AACTCCACCA CAGAGCACCA GCAAT    35

( 2 ) INFORMATION FOR SEQ ID NO: 24:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 24:

ATTGCTGGTG CTCTGTGGTG GAGTTTTCCT GCCACTCA    38

( 2 ) INFORMATION FOR SEQ ID NO: 25:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 25:

GTGGCACTGA AACTCCACCA CAGAGCACCA GCAGT    35

( 2 ) INFORMATION FOR SEQ ID NO: 26:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: irrelevant ( i v ) ANTI-SENSE: no ( i x ) SEQUENCE DESCRIPTION:SEQ ID NO: 26:

ACTGCTGGTG CTCTGTGGTG GAGTTTCAGT GCCACTCA    38

( 2 ) INFORMATION FOR SEQ ID NO: 27:

( i ) SEQUENCE CHARACTERISTICS:
        ( A ) LENGTH: 35 base pairs
        ( B ) TYPE: nucleic acid
        ( C ) STRANDEDNESS: single (D) TOPOLOGY: linear (ii) MOLECULE TYPE: genomic DNA (iii) HYPOTHETICAL: irrelevant (iv) ANTI-SENSE: no (ix) SEQUENCE DESCRIPTION:SEQ ID NO: 27:

GTGGCATTGG GATTCCACCA CAGAGCACCA GCAGT                35

(2) INFORMATION FOR SEQ ID NO: 28:

(i) SEQUENCE CHARACTERISTICS:
    (A) LENGTH: 38 base pairs
    (B) TYPE: nucleic acid
    (C) STRANDEDNESS: single
    (D) TOPOLOGY: linear (ii) MOLECULE TYPE: genomic DNA (iii) HYPOTHETICAL: irrelevant (iv) ANTI-SENSE: no (ix) SEQUENCE DESCRIPTION:SEQ ID NO: 28:

ACTGCTGGTG CTCTGTGGTG GAATCCCAAT GCCACTCA             38

(2) INFORMATION FOR SEQ ID NO: 29:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (ii) MOLECULE TYPE: genomic DNA (iii) HYPOTHETICAL: irrelevant (iv) ANTI-SENSE: no (ix) SEQUENCE DESCRIPTION:SEQ ID NO: 29:

TGCTGCAGAA CTCCCAGCTG TACCTCCTCG CCTTAAAGAC G         41

(2) INFORMATION FOR SEQ ID NO: 30:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: genomic DNA (iii) HYPOTHETICAL: irrelevant (iv) ANTI-SENSE: no (ix) SEQUENCE DESCRIPTION:SEQ ID NO: 30:

GCTGTTCCAG GGGGTGCACT CG                              22

(2) INFORMATION FOR SEQ ID NO: 31:

(i) SEQUENCE CHARACTERISTICS:
    (A) LENGTH: 50 amino acids
    (B) TYPE: amino acids
    (D) TOPOLOGY: linear (ii) MOLECULE TYPE: protein (ix) FEATURE:
    (A) NAME/KEY: signal sequence
    (B) LOCATION: 1-50 amino acids from N-terminus (C) IDENTIFICATION METHOD: similarity to other sequences, hydrophobic
(D) OTHER INFORMATION: human tissue plasminogen activator (TPA)

(xi) SEQUENCE DESCRIPTION:SEQ ID NO: 31:

Ser Tyr Gln Val Ile Cys Arg Asp Glu Lys Tyr Gln Met Ile
                    5                   10

Tyr Gln Gln His Gln Ser Trp Leu Arg Pro Val Leu Arg Ser
 15              20                  25

Asn Arg Val Glu Tyr Cys Trp Cys Asn Ser Gly Arg Ala Gln
     30              35                  40

Cys His Ser Val Pro Val Lys Ser
         45              50

(2) INFORMATION FOR SEQ ID NO: 32:

(i) SEQUENCE CHARACTERISTICS:
(A) LENGTH: 13 amino acids
(B) TYPE: amino acids
(D) TOPOLOGY: linear (ii) MOLECULE TYPE: protein (ix) FEATURE:
(A) NAME/KEY: signal sequence
(B) LOCATION: 7-19 amino acids from N-terminus
(C) IDENTIFICATION METHOD: similarity to other sequences
(D) OTHER INFORMATION: a human tissue plasminogen activator variant (xi) SEQUENCE DESCRIPTION:SEQ ID NO: 32:

Lys Lys Lys Lys Tyr Gln Met Ile Tyr Gln Gln His Gln
             10                  15

(2) INFORMATION FOR SEQ ID NO: 33:

(i) SEQUENCE CHARACTERISTICS:
(A) LENGTH: 13 amino acids
(B) TYPE: amino acids
(D) TOPOLOGY: linear (ii) MOLECULE TYPE: protein (ix) FEATURE:
(A) NAME/KEY: signal sequence
(B) LOCATION: 7-19 amino acids from N-terminus
(C) IDENTIFICATION METHOD:similarity to other sequences
(D) OTHER INFORMATION: a human tissue plasminogen activator variant (xi) SEQUENCE DESCRIPTION:SEQ ID NO: 33:

Arg Asp Glu Glu Val Ser Ser Ser Tyr Gln Gln His Gln
             10                  15

(2) INFORMATION FOR SEQ ID NO: 34:

(i) SEQUENCE CHARACTERISTICS:
(A) LENGTH: 13 amino acids
(B) TYPE: amino acids
(D) TOPOLOGY: linear (ii) MOLECULE TYPE: protein (ix) FEATURE:
(A) NAME/KEY: signal sequence
(B) LOCATION: 7-19 amino acids from N-terminus
(C) IDENTIFICATION METHOD:similarity to other sequences
(D) OTHER INFORMATION: a human tissue plasminogen activator variant (xi) SEQUENCE DESCRIPTION:SEQ ID NO: 34:

Arg Asp Glu Lys Tyr Gln Met Ile Phe Ser Ser Glu Ser
             10                          15

( 2 ) INFORMATION FOR SEQ ID NO: 35:

( i ) SEQUENCE CHARACTERISTICS:
        ( A ) LENGTH: 6 amino acids
        ( B ) TYPE: amino acids
        ( D ) TOPOLOGY: linear ( i i ) MOLECULE TYPE: protein ( i x ) FEATURE:
        ( A ) NAME/KEY: signal sequence
        ( B ) LOCATION: 28-33 amino acids from N-terminus
        ( C ) IDENTIFICATION METHOD:similarity to other sequences
        ( D ) OTHER INFORMATION: a human tissue plasminogen activator
                                                        variant ( x i ) SEQUENCE DESCRIPTION:SEQ ID NO: 35:

Val Ser Glu Ser Lys Asn
         30

( 2 ) INFORMATION FOR SEQ ID NO: 36:

( i ) SEQUENCE CHARACTERISTICS:
        ( A ) LENGTH: 10 amino acids
        ( B ) TYPE: amino acids
        ( D ) TOPOLOGY: linear ( i i ) MOLECULE TYPE: protein ( i x ) FEATURE:
        ( A ) NAME/KEY: signal sequence
        ( B ) LOCATION: 35-44 amino acids from N-terminus
        ( C ) IDENTIFICATION METHOD:similarity to other sequences
        ( D ) OTHER INFORMATION: a human tissue plasminogen activator
                                                        variant ( x i ) SEQUENCE DESCRIPTION:SEQ ID NO: 36:

Trp Cys Ser Val Val Glu Ser Ser Cys His
35                       40

( 2 ) INFORMATION FOR SEQ ID NO: 37:

( i ) SEQUENCE CHARACTERISTICS:
        ( A ) LENGTH: 10 amino acids
        ( B ) TYPE: amino acids
        ( D ) TOPOLOGY: linear ( i i ) MOLECULE TYPE: protein ( i x ) FEATURE:
        ( A ) NAME/KEY: signal sequence
        ( B ) LOCATION: 35-44 amino acids from N-terminus
        ( C ) IDENTIFICATION METHOD:similarity to other sequences
        ( D ) OTHER INFORMATION: a human tissue plasminogen activator
                                                        variant ( x i ) SEQUENCE DESCRIPTION:SEQ ID NO: 37:

Trp Cys Leu Val Val Ile Val Leu Cys His
35                       40

( 2 ) INFORMATION FOR SEQ ID NO: 38:

( i ) SEQUENCE CHARACTERISTICS:
        ( A ) LENGTH: 10 amino acids
        ( B ) TYPE: amino acids
        ( D ) TOPOLOGY: linear ( i i ) MOLECULE TYPE: protein ( i x ) FEATURE:
        ( A ) NAME/KEY: signal sequence
        ( B ) LOCATION: 35-44 amino acids from N-terminus -continued ( C ) IDENTIFICATION METHOD:similarity to other sequences
          ( D ) OTHER INFORMATION: a human tissue plasminogen activator
                                                    variant ( x i ) SEQUENCE DESCRIPTION:SEQ ID NO: 38:

Trp  Cys  Ser  Val  Val  Ile  Ser  Ser  Cys  His
3 5                            4 0

( 2 ) INFORMATION FOR SEQ ID NO: 39:

( i ) SEQUENCE CHARACTERISTICS:
          ( A ) LENGTH: 10 amino acids
          ( B ) TYPE: amino acids
          ( D ) TOPOLOGY: linear ( i i ) MOLECULE TYPE: protein ( i x ) FEATURE:
          ( A ) NAME/KEY: signal sequence
          ( B ) LOCATION: 35-44 amino acids from N-terminus
          ( C ) IDENTIFICATION METHOD:similarity to other sequences
          ( D ) OTHER INFORMATION: a human tissue plasminogen activator
                                                    variant ( x i ) SEQUENCE DESCRIPTION:SEQ ID NO: 39:

Trp  Cys  Ser  Val  Val  Ile  Val  Ser  Cys  His
3 5                            4 0

( 2 ) INFORMATION FOR SEQ ID NO: 40:

( i ) SEQUENCE CHARACTERISTICS:
          ( A ) LENGTH: 10 amino acids
          ( B ) TYPE: amino acids
          ( D ) TOPOLOGY: linear ( i i ) MOLECULE TYPE: protein ( i x ) FEATURE:
          ( A ) NAME/KEY: signal sequence
          ( B ) LOCATION: 35-44 amino acids from N-terminus
          ( C ) IDENTIFICATION METHOD:similarity to other sequences
          ( D ) OTHER INFORMATION: a human tissue plasminogen activator
                                                    variant ( x i ) SEQUENCE DESCRIPTION:SEQ ID NO: 40:

Trp  Cys  Ser  Val  Val  Ile  Val  Leu  Cys  His
3 5                            4 0

( 2 ) INFORMATION FOR SEQ ID NO: 41:

( i ) SEQUENCE CHARACTERISTICS:
          ( A ) LENGTH: 10 amino acids
          ( B ) TYPE: amino acids
          ( D ) TOPOLOGY: linear ( i i ) MOLECULE TYPE: protein ( i x ) FEATURE:
          ( A ) NAME/KEY: signal sequence
          ( B ) LOCATION: 35-44 amino acids from N-terminus
          ( C ) IDENTIFICATION METHOD:similarity to other sequences
          ( D ) OTHER INFORMATION: a human tissue plasminogen activator
                                                    variant ( x i ) SEQUENCE DESCRIPTION:SEQ ID NO: 41:

Trp  Cys  Phe  Leu  Phe  Val  Leu  Phe  Cys  His
3 5                            4 0

( 2 ) INFORMATION FOR SEQ ID NO: 42:

( i ) SEQUENCE CHARACTERISTICS:
          ( A ) LENGTH: 10 amino acids
          ( B ) TYPE: amino acids
          ( D ) TOPOLOGY: linear ( i i ) MOLECULE TYPE: protein ( i x ) FEATURE:
                ( A ) NAME/KEY: signal sequence
                ( B ) LOCATION: 35-44 amino acids from N-terminus
                ( C ) IDENTIFICATION METHOD:similarity to other sequences
                ( D ) OTHER INFORMATION: a human tissue plasminogen activator
                                                            variant ( x i ) SEQUENCE DESCRIPTION:SEQ ID NO: 42:

Trp Cys Val Phe Leu Phe Ile Val Cys His
3 5                     4 0

( 2 ) INFORMATION FOR SEQ ID NO: 43:

( i ) SEQUENCE CHARACTERISTICS:
                ( A ) LENGTH: 10 amino acids
                ( B ) TYPE: amino acids
                ( D ) TOPOLOGY: linear ( i i ) MOLECULE TYPE: protein ( i x ) FEATURE:
                ( A ) NAME/KEY: signal sequence
                ( B ) LOCATION: 35-44 amino acids from N-terminus
                ( C ) IDENTIFICATION METHOD:similarity to other sequences
                ( D ) OTHER INFORMATION: a human tissue plasminogen activator
                                                            variant ( x i ) SEQUENCE DESCRIPTION:SEQ ID NO: 43:

Trp Cys Ser Val Val Glu Phe Ser Cys His
3 5                     4 0

( 2 ) INFORMATION FOR SEQ ID NO: 44:

( i ) SEQUENCE CHARACTERISTICS:
                ( A ) LENGTH: 10 amino acids
                ( B ) TYPE: amino acids
                ( D ) TOPOLOGY: linear ( i i ) MOLECULE TYPE: protein ( i x ) FEATURE:
                ( A ) NAME/KEY: signal sequence
                ( B ) LOCATION: 35-44 amino acids from N-terminus
                ( C ) IDENTIFICATION METHOD:similarity to other sequences
                ( D ) OTHER INFORMATION: a human tissue plasminogen activator
                                                            variant ( x i ) SEQUENCE DESCRIPTION:SEQ ID NO: 44:

Trp Cys Ser Val Val Glu Phe Gln Cys His
3 5                     4 0

( 2 ) INFORMATION FOR SEQ ID NO: 45:

( i ) SEQUENCE CHARACTERISTICS:
                ( A ) LENGTH: 10 amino acids
                ( B ) TYPE: amino acids
                ( D ) TOPOLOGY: linear ( i i ) MOLECULE TYPE: protein ( i x ) FEATURE:
                ( A ) NAME/KEY: signal sequence
                ( B ) LOCATION: 35-44 amino acids from N-terminus
                ( C ) IDENTIFICATION METHOD:similarity to other sequences
                ( D ) OTHER INFORMATION: a human tissue plasminogen activator
                                                            variant ( x i ) SEQUENCE DESCRIPTION:SEQ ID NO: 45:

Trp Cys Ser Val Val Glu Ser Gln Cys His
3 5                     4 0

1. A human tissue plasminogen activator variant wherein each of amino acid positions 37–42 (Asn-Ser- 2. A human tissue plasminogen activator variant according to claim 1 wherein amino acid positions 37–42 are replaced by serine, valine, valine, glutamic acid, serine, and serine, respectively.

3. A human tissue plasminogen activator variant according to claim 1 wherein amino acid positions 37–42 are replaced by serine, valine, valine, glutamic acid, phenylalanine, and serine, respectively.

4. A human tissue plasminogen activator variant according to claim 1 wherein amino acids positions 37–42 are replaced by serine, valine, valine, isoleucine, valine, serine, respectively.

5. A human tissue plasminogen activator variant wherein amino acid position 161 (Gly), amino acid position 162 (Lys), and amino acid position 165 (Ser) of the mature human tissue plasminogen activator are replaced by arginine, arginine, and tryptophan, respectively.

6. A human tissue plasminogen activator variant wherein each of amino acid positions 37–42 (Asn-Ser-Gly-Arg-Ala-Gln), amino acid position 161 (Gly), amino acid position 162 (Lys), and amino acid position 165 (Ser) of the mature human tissue plasminogen activator is replaced by serine, valine, valine, glutamic acid, phenylalanine, serine, arginine, arginine, and tryptophan, respectively.

7. A human plasminogen activator variant wherein each of amino acid positions 37–42 (Asn-Ser-Gly-Arg-Ala-Gln) and amino acid position 115 (Asn) of the mature human tissue plasminogen activator is replaced by serine, valine, valine, glutamic acid, phenylalanine, serine, and proline, respectively.

8. An isolated DNA sequence encoding the human tissue plasminogen activator variant of claim 1, 2, 3, 4, 5, 6, or 7.

9. An expression vector comprising a DNA sequence of claim 8 and a regulatory region operably linked to said DNA sequence.

10. A cultured animal host cell transformed by the expression vector of claim 9.

11. The host cell of claim 10 which is a Chinese hamster ovary (CHO) cell.

12. A glycosylated human tissue plasminogen activator variant obtained by culturing the host cell of claim 10 under conditions suitable for expression and recovering the produced protein.

13. A method for producing a human tissue plasminogen activator comprising the steps of constructing an expression vector which comprises the DNA sequence of claim 8, transforming a cultured animal host cell with the vector, culturing the transformed host cell under conditions suitable to produce the human tissue plasminogen activator variant, and recovering the produced human tissue plasminogen activator variant.

* * * * *

UNITED STATES PATENT AND TRADEMARK OFFICE
CERTIFICATE OF CORRECTION

PATENT NO. : 5,407,819
DATED : April 18, 1995
INVENTOR(S) : Hitoshi Yahara, Tetsuya Nagaoka, Kazuyoshi Yajima, Yasuhiro Ikenaka Keiji Matsumoto, Tetsu Kakutani Page 1 of 2

It is certified that error appears in the above-indentified patent and that said Letters Patent is hereby corrected as shown below: On the title page: Item [76]

delete "Inenaka" and replace thereto --Ikenaka--

Column 17, Table 1, add -- - -- before the phrase "denote the same amino acid as that of TPA"

Column 28, Line 8, delete " ; rTPA, ;PN1; : PN2, ; PN3, ;DS1, ;" and replace thereto --○; rTPA,□; PN1; △; PN2, ●; PN3,■ ; DS1,▲;--

Column 28, Line 12, delete " ; rTPA, ; KM21, ;" and replace thereto --○; rTPA,●; KM21,■;--

Column 28, Line 13, delete "KM4, ;" and replace thereto --KM4,▲;--

Column 28, Line 16, delete " ; rTPA, ;" and replace thereto --○; rTPA,▲;--

UNITED STATES PATENT AND TRADEMARK OFFICE
CERTIFICATE OF CORRECTION

PATENT NO. : 5,407,819
DATED : April 18, 1995
INVENTOR(S) : Hitoshi Yahara, Tetsuya Nagaoka, Kazuyoshi Yajima, Yasuhiro Ikenaka, Keiji Matsumoto, Tetsu Kakutani It is certified that error appears in the above-indentified patent and that said Letters Patent is hereby corrected as shown below:

Column 28, Line 17, delete " ; SD9, ;" and replace thereto
-- ●; SD9, ■ ;--

Column 49, after (Asn-Ser-, add --Gly -Arg-Ala-Gln) of the mature human tissue plasminogen activator is replaced by any amino acid selected from the group consisting of phenylalanine, valine, isoleucine, leucine, glutamic acid and serine--

Column 27, Line 30, delete " ; 140 ng/ml," and replace thereto
-- ▲ ; 140 ng/ml,--

Column 27, Line 31, delete " ; 200 ng/ml, ; 500 ng/ml, ;" and replace thereto -- ○ ; 200 ng/ml, ● ; 500 ng/ml, ■ ;--

Signed and Sealed this

Twenty-sixth Day of September, 1995

Attest:

BRUCE LEHMAN

Attesting Officer

Commissioner of Patents and Trademarks